United States Patent
Roh et al.

(10) Patent No.: US 12,089,905 B1
(45) Date of Patent: Sep. 17, 2024

(54) COMPUTERIZED CONTROL AND NAVIGATION OF A ROBOTIC SURGICAL APPARATUS

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 18/321,084

(22) Filed: May 22, 2023

(51) Int. Cl.
*A61B 34/30* (2016.01)
*A61B 34/00* (2016.01)
*A61B 34/10* (2016.01)
*A61B 34/20* (2016.01)

(52) U.S. Cl.
CPC .............. *A61B 34/30* (2016.02); *A61B 34/10* (2016.02); *A61B 34/20* (2016.02); *A61B 34/25* (2016.02); *A61B 2034/2055* (2016.02); *A61B 2034/252* (2016.02)

(58) Field of Classification Search
CPC ......... A61B 34/30; A61B 34/10; A61B 34/20; A61B 34/25; A61B 2034/2055
See application file for complete search history.

(56) References Cited

U.S. PATENT DOCUMENTS

| | | | |
|---|---|---|---|
| 11,304,760 B1* | 4/2022 | Roh | A61F 7/0097 |
| 11,357,582 B1* | 6/2022 | Roh | G10L 13/02 |
| 11,389,248 B1* | 7/2022 | Roh | G05B 13/0265 |
| 2018/0333207 A1* | 11/2018 | Moctezuma De la Barrera | A61B 34/25 |
| 2019/0069962 A1* | 3/2019 | Tabandeh | A61B 34/25 |
| 2022/0031412 A1* | 2/2022 | Roldan | A61B 34/30 |

* cited by examiner

*Primary Examiner* — James M Kish
*Assistant Examiner* — Roland Dinga
(74) *Attorney, Agent, or Firm* — Perkins Coie LLP

(57) ABSTRACT

The present disclosure provides a method for a surgical robot with extended operational range in which a user inputs the surgical robot's movements and locations in a CAD environment through a surgical robot network and the surgical robot movements and locations are stored as a data file. The surgical robot network sends the surgical robot movements and locations data files to the surgical robot which extracts the data file containing the surgical robot movements and locations. The surgical robot then executes the data files containing the surgical robot movements and locations and sends a completion status of the movements and locations and the surgical robot executes a data file containing the robotic movements to perform aspects of the surgical procedure.

20 Claims, 18 Drawing Sheets

| Patient ID | Surgery | 3D Image | Starting Location | Ending Location | Movement Data File | Process | Techniques | Tools Required | Procedure Data File | Calculations - Force | Calculations - Materials | Calculations - Specialist |
|---|---|---|---|---|---|---|---|---|---|---|---|---|
| JS123 | Brostrom-Gould Repair Surgery | JS123Ankle 3D.data | Storage Position | Left Side of Patient, Leg Level | Movement#1.Data | Mark spots on skin for anchors and suture locations on extensor retinaculum | - | None | Process1.data | - | - | orthopedic foot surgeon |
| | | | Left Side of Patient, Leg Level | Left Side of Patient, Leg Level | N/A | make incision at distal point of fibula | - | Knife | Process2.data | - | - | orthopedic foot surgeon |
| | | | Left Side of Patient, Leg Level | Left Side of Patient, Leg Level | N/A | use forceps to open incision | - | Basket Forceps | Process3.data | - | - | orthopedic foot surgeon |
| | | | Left Side of Patient, Leg Level | Left Side of Patient, Leg Level | N/A | separate extensor retinaculum from fibula | - | Knife | Process4.data | - | - | orthopedic foot surgeon |
| | | | Left Side of Patient, Leg Level | Left Side of Patient, Leg Level | N/A | remove cortical surface of fibula | - | Knife | Process5.data | - | - | orthopedic foot surgeon |
| | | | Left Side of Patient, Leg Level | Right Side of Patient, Leg Level | Movement2.Data | place drill guide | - | Drill | Process6.data | - | - | orthopedic foot surgeon |
| | | | Right Side of Patient, Leg Level | Right Side of Patient, Leg Level | N/A | use drill guide to drill into fibula | - | Drill | Process7.data | .5PSi | - | orthopedic foot surgeon |
| | | | Right Side of Patient, Leg Level | Right Side of Patient, Leg Level | N/A | use drill guide to place suture anchor | - | Anchors | Process8.data | - | - | orthopedic foot surgeon |
| | | | Right Side of Patient, Leg Level | Left Side of Patient, Leg Level | Movement3.Data | | fibula anchor – suture through extensor retinaculum once and return to anchor | Suture | Technique1.data | - | synthetic polymer fibers | orthopedic foot surgeon |
| | | | Left Side of Patient, Leg Level | Left Side of Patient, Leg Level | N/A | | calcaneus anchor – suture through extensor retinaculum four times in a weaving fashion and return to fibula anchor | Suture | Technique2.data | - | synthetic polymer fibers | orthopedic foot surgeon |

*FIG. 14*

| Patient ID | Surgery | 3D Image | Starting Location | Ending Location | Movement Data File | Process | Techniques | Tools Required | Procedure Data File | Force | Materials | Specialist |
|---|---|---|---|---|---|---|---|---|---|---|---|---|
| JS123 | Brostrom-Gould Repair Surgery | JS123Ankle 3D.data | Storage Position | Left Side of Patient, Leg Level | Movement#1. Data | Mark spots on skin for anchors and suture locations on extensor retinaculum | - | None | Process1.data | - | - | orthopedic foot surgeon |
| | | | Left Side of Patient, Leg Level | Left Side of Patient, Leg Level | N/A | make incision at distal point of fibula | - | Knife | Process2.data | - | - | orthopedic foot surgeon |
| | | | Left Side of Patient, Leg Level | Left Side of Patient, Leg Level | N/A | use forceps to open incision | - | Basket Forceps | Process3.data | - | - | orthopedic foot surgeon |
| | | | Left Side of Patient, Leg Level | Left Side of Patient, Leg Level | N/A | separate extensor retinaculum from fibula | - | Knife | Process4.data | - | - | orthopedic foot surgeon |
| | | | Left Side of Patient, Leg Level | Left Side of Patient, Leg Level | N/A | remove cortical surface of fibula | - | Knife | Process5.data | - | - | orthopedic foot surgeon |
| | | | Left Side of Patient, Leg Level | Right Side of Patient, Leg Level | Movement2. Data | place drill guide | - | Drill | Process6.data | - | - | orthopedic foot surgeon |
| | | | Right Side of Patient, Leg Level | Right Side of Patient, Leg Level | N/A | use drill guide to drill into fibula | - | Drill | Process7.data | .5PSI | - | orthopedic foot surgeon |
| | | | Right Side of Patient, Leg Level | Right Side of Patient, Leg Level | N/A | use drill guide to place suture anchor | - | Anchors | Process8.data | - | - | orthopedic foot surgeon |
| | | | Right Side of Patient, Leg Level | Left Side of Patient, Leg Level | Movement3. Data | | fibula anchor – suture through extensor retinaculum once and return to anchor | Suture | Technique1. data | - | synthetic polymer fibers | orthopedic foot surgeon |
| | | | Left Side of Patient, Leg Level | Left Side of Patient, Leg Level | N/A | | calcaneus anchor – suture through extensor retinaculum four times in a weaving fashion and return to fibula anchor | Suture | Technique2. data | - | synthetic polymer fibers | orthopedic foot surgeon |

FIG. 17

COMPUTERIZED CONTROL AND NAVIGATION OF A ROBOTIC SURGICAL APPARATUS

TECHNICAL FIELD

The present disclosure is generally related to automated and robotic surgical procedures and specifically to surgical robot apparatuses with extended operational range.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure, as well as technical surgical errors during the operation. For example, adverse events can occur due to (i) a breakdown in communication within and among the surgical team, care providers, patients, and their families; (ii) delays in diagnosis or failure to diagnose; and (iii) delays in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 14 illustrates a surgery database, according to an embodiment.

FIG. 17 illustrates a procedure database, according to an embodiment.

DETAILED DESCRIPTION

Figure 1:
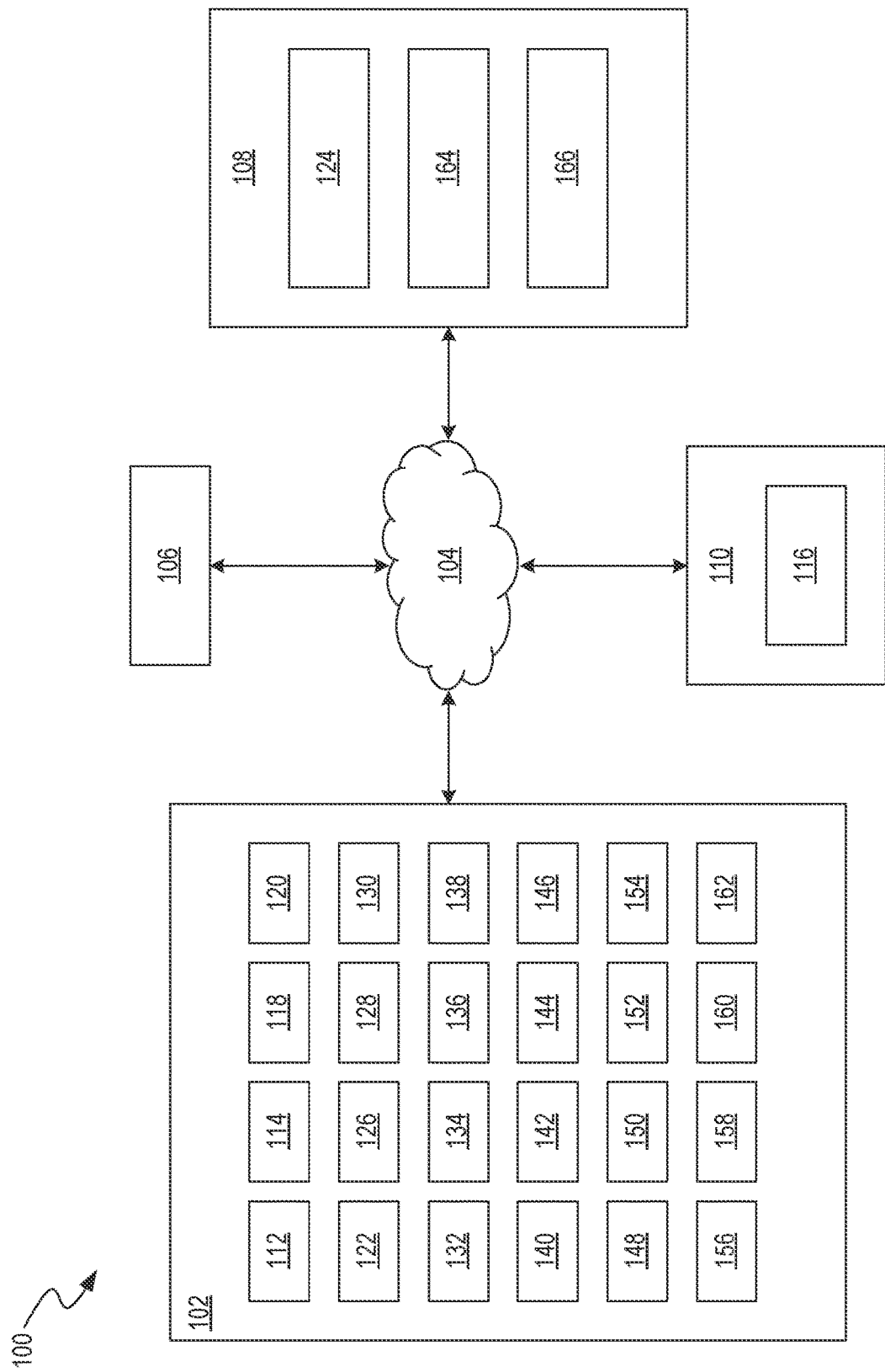
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610a") described as a single instance. Further, plural instances (e.g., "610") refer collectively to a set of components, operations, or structures (e.g., "610a") described as a single instance. The description of a single component (e.g., "610a") applies equally to a like-numbered component (e.g., "610b") unless indicated otherwise. These and other aspects, features, and implementations can be expressed as methods, apparatuses, systems, components, program products, means or steps for performing a function, and in other ways. These and other aspects, features, and implementations will become apparent from the following descriptions, including the claims.

Robotic surgeries are types of surgical procedures that are done using robotic systems. Robotically assisted surgery was developed to try to overcome the limitations of pre-existing minimally-invasive surgical procedures and to enhance the capabilities of surgeons performing open surgery. In the case of robotically-assisted, minimally-invasive surgery, instead of directly moving the instruments, the surgeon uses one of two methods to administer the instruments. These include using a direct telemanipulator or through computer control. A telemanipulator is a remote manipulator that allows the surgeon to perform the normal movements associated with the surgery. The robotic arms carry out those movements using end-effectors and manipulators to perform the actual surgery. In computer-controlled systems, the surgeon uses a computer to control the robotic arms and its end-effectors, though these systems can also still use telemanipulators for their input. An advantage of using the computerized method is that the surgeon does not have to be present, leading to the possibility for remote surgery.

Memory devices can play an essential role in preventing inconveniences in the robot-assisted surgery. The memory storage solutions can perform multiple functions based on the patient's physical record. They can also indicate specific information to measure calibration offsets indicating misalignment of the storage drive system, life of the data, and so on.

The embodiments disclosed herein describe methods and systems for surgical robot apparatuses with extended operational range. The disclosed systems enable surgical robots having an extended operational range. A user inputs a surgical robot's movements and locations in a computer-aided design (CAD) environment through a surgical robot network. The surgical robot movements and locations are stored as a data file. The surgical robot network sends the surgical robot movements and locations data files to the surgical robot, which extracts the data file containing the surgical robot movements and locations. The surgical robot then executes the data files containing the surgical robot movements and locations and sends a completion status of the movements and locations. The surgical robot executes a data file containing the robotic movements to perform aspects of the surgical procedure.

In embodiments, a method for relocating a base of a robotic assisted surgery device includes providing a robotic assisted surgery device in an operating room. The robotic assisted surgery device includes at least one end-effector attached to a robotic arm and a mobile base capable of relocating the robotic assisted surgery device in the operating room. The robotic assisted surgery device is positioned in a first location in the operating room. Instructions to relocate the robotic assisted surgery device to a second location in the operating room are generated. The instructions are executed and the robotic assisted surgery device is relocated to a second location in the operating room. Relocating the robotic assisted surgery device provides extended operational range to at least one end-effector of the robotic assisted surgery device.

In embodiments, medical imaging is performed using different wavelengths of electromagnetic energy, ultrasounds, magnetic resonance, etc. The different wavelengths when directed towards a subject, such as bone tissue, soft tissue, or any other subject or substance, image different types of tissues with varying depths of penetration. For example, when visible light of a predefined wavelength is directed at bone tissue, a part of the incident light can be absorbed by the bone tissue. As a result, the intensity of the reflected/refracted light is less than that of the incident light. The decrease in the intensity of the incident light can be measured and used to generate an image. In embodiments, different medical devices having capabilities including, but not limited to, X-ray imaging, magnetic resonance imaging (MRI), ultrasound, angiography, or computed tomography (CT) are used. In embodiments, omni-tomographic imaging or grand fusion imaging, such as large-scale fusion of simultaneous data acquisition from multiple imaging modalities (e.g., CT, MRI, positron emission tomography (PET), SPECT, USG, or optical imaging), is used. Composite images, including image data from multiple modalities, are sometimes referred to as "multi-modality images" or "multiple-modality images" herein.

In embodiments, the disclosed systems use a surgical robot network that receives medical images of a patient and generates a three-dimensional (3D) rendering of the various medical images. A surgeon or physician is enabled to select workflow objects (such as various tools). The workflow objects can be selected in a sequence for performing actions on the 3D rendering. Data related to the workflow objects and actions in relation to the 3D rendering are stored. The surgeon or physician is enabled to select and perform various threading techniques and input calculations of the actions performed. The user's inputs, workflow objects, and actions with respect to the 3D rendering are sent to a surgical robot for performing robotic joint arthroscopic surgery.

In embodiments, a robotic surgical system uses machine learning (ML) to provide recommendations and methods for automated robotic ankle arthroscopic surgery. Historical patient data is filtered to match particular parameters of a patient. The parameters are correlated to the patient. A robotic surgical system or a surgeon reviews the historical patient data to select or adjust the historical patient data to generate a surgical workflow for a surgical robot for performing the robotic arthroscopic surgery.

In some embodiments, a surgical robot receives user inputs, workflow objects, and data files containing surgical actions for robotic movements from a surgery network. Information describing surgical tools required for performing the robotic arthroscopic surgery are displayed on a user interface for the surgical tools to be enabled or disabled. Information describing the robotic arthroscopic surgical steps are displayed on the user interface in a sequence to enable execution of the data files containing the robotic movements. The robotic movements are used to perform surgical steps or assist a surgeon in performing surgical steps.

In some embodiments, the disclosed systems can perform an arthroscopic surgical procedure on a joint of a patient. The system can acquire data (e.g., user input, patient data, etc.) from user interfaces and storage devices. An ML algorithm can analyze the patient data to determine one or more ligament-attachment joint stabilization steps for the joint. The system can generate a robotic-enabled surgical plan for the joint based on the user input and the one or more ligament-attachment joint stabilization steps. In some implementations, the robotic-enabled surgical plan includes a sequence of surgical steps with corresponding surgical tools for attaching one or more connectors to at least one ligament of the joint and another structure of the patient to promote stabilization of the joint. A GUI can display the robotic-enabled surgical plan for intraoperative viewing by a user (e.g., healthcare provider) while the robotic surgical system robotically operates on the patient. The system can receive, from the user, intraoperative user input associated with one or more of the surgical steps of the robotic-enabled surgical plan. The system determines information to be displayed, via the GUI, based on the received intraoperative user input while controlling one or more of the tools operated by the robotic surgical system according to a selection.

The advantages and benefits of the methods, systems, and apparatuses disclosed herein include compatibility with best practice guidelines for performing surgery in an operating room, e.g., from regulatory bodies and professional standards organizations such as the Association for Surgical Technologists. The imaging systems disclosed use computer networks, the Internet, intranets, and supporting technologies to implement a cost-effective technology to collect, transmit, store, analyze, and use imaging information in electronic formats. As a result, surgical robots can use the embodiments to collect and analyze vast amounts of information, resulting in early diagnoses. The disclosed methods reduce the amount of noise and increase the resolution, replicability, efficiency, and accuracy in collecting and analyzing information. Further, the embodiments disclosed herein enable meta-analyses for more-elaborate diagnostic procedures and reduce the need for repetitive invasive diagnostic testing. In addition, the disclosed systems enable continuous monitoring and analysis of the health of the patient in order to provide real-time assistance to a surgical robot or surgeon during a surgical procedure.

The technologies disclosed improve placement of surgical robots, location of surgical robots, and positioning of patients for surgical procedures compared to traditional technologies. Moreover, the disclosed methods are beneficial in repositioning or relocating surgical robots during surgical procedures compared to traditional methods. The disclosed apparatuses provide computer-aided design (CAD) ability to surgeons and physicians to enable them to manipulate a 3D rendering of a region of a patient's anatomy to virtually perform surgery. The disclosed methods provide a workflow process based on CAD software to improve chances of success of detailed steps of a surgical procedure. The disclosed systems enable surgeons to perform virtual surgeries using a robotic system to generate optimal results for a patient, especially for robotic joint arthroscopic surgery for the lateral EDL tendon area of the anatomy.

Further, the embodiments provide automated and more efficient systems for using multiple imaging modalities, especially those using different wavelengths of electromagnetic waves. Quicker diagnosis of patients is achieved compared to traditional methods via simultaneous or sequential imaging. The automated methods of aligning images taken using different imaging modalities disclosed provided improved analysis of the images to identify medical conditions. In addition, the advantages of the convolutional neural network (CNN) used for ML in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or an outpatient surgery center.

In some embodiments, the system 100 includes one or more medical or surgical patient monitors 112. The monitors 112 can include a vital signs monitor (a medical diagnostic instrument), which can be a portable, battery-powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the body part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end-tidal CO2 monitor or capnography monitor used for measurement of the level of carbon dioxide that is released at the end of an exhaled breath (referred to as end-tidal carbon dioxide, ETCO2). An end-tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal CO2 monitor can be configured as side stream (diverting) or mainstream (non-diverting). A diverting end-tidal CO2 monitor transports a portion of a patient's respired gases from the sampling site to the end-tidal CO2 monitor, while a non-diverting end-tidal CO2 monitor does not transport gas away. Also, measurement by the end-tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in an artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as the bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality (AR) device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably two-dimensional (2D) or three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Two-dimensional (2D) or three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles 126, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument 130 can consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, MRI, ultrasound, endoscopy, elastography, tactile imaging, thermography, medical photography, and nuclear medicine, e.g., PET. Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used are brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses CT imaging that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where it is working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (02), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The SCD 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. A CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR is a digital version of patients' paper charts. The EHR database 106 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

In embodiments, the system 100 uses quantum computing. Quantum computing refers to the use of a computational device or method that uses properties of quantum states defined by quantum mechanics such as superposition, entanglement, etc., to perform computations. Quantum devices use qubits, which are the quantum equivalent of bits in a classical computing system. Qubits have at least two quantum states or probable outcomes. These outcomes, combined with a coefficient representing the probability of each outcome, describes the possible states, or bits of data, which can be represented by the qubits according to the principle of quantum superposition. These states can be manipulated to shift the probability of each outcome, or additionally, add additional possible outcomes to perform computations, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows the greatest promise for drug discovery and simulating the interaction of drugs with biologic systems, however the same technology can also be used to predict the interaction of a biologic system with an implanted device, preventing rejection of an implant by a patient's body. Quantum computing can be used to investigate long term functioning of an implant. Further, quantum computing can be used to study the reaction of a patient to a surgical procedure, during a simulation, before a procedure, or actively during a procedure.

Figure 2:
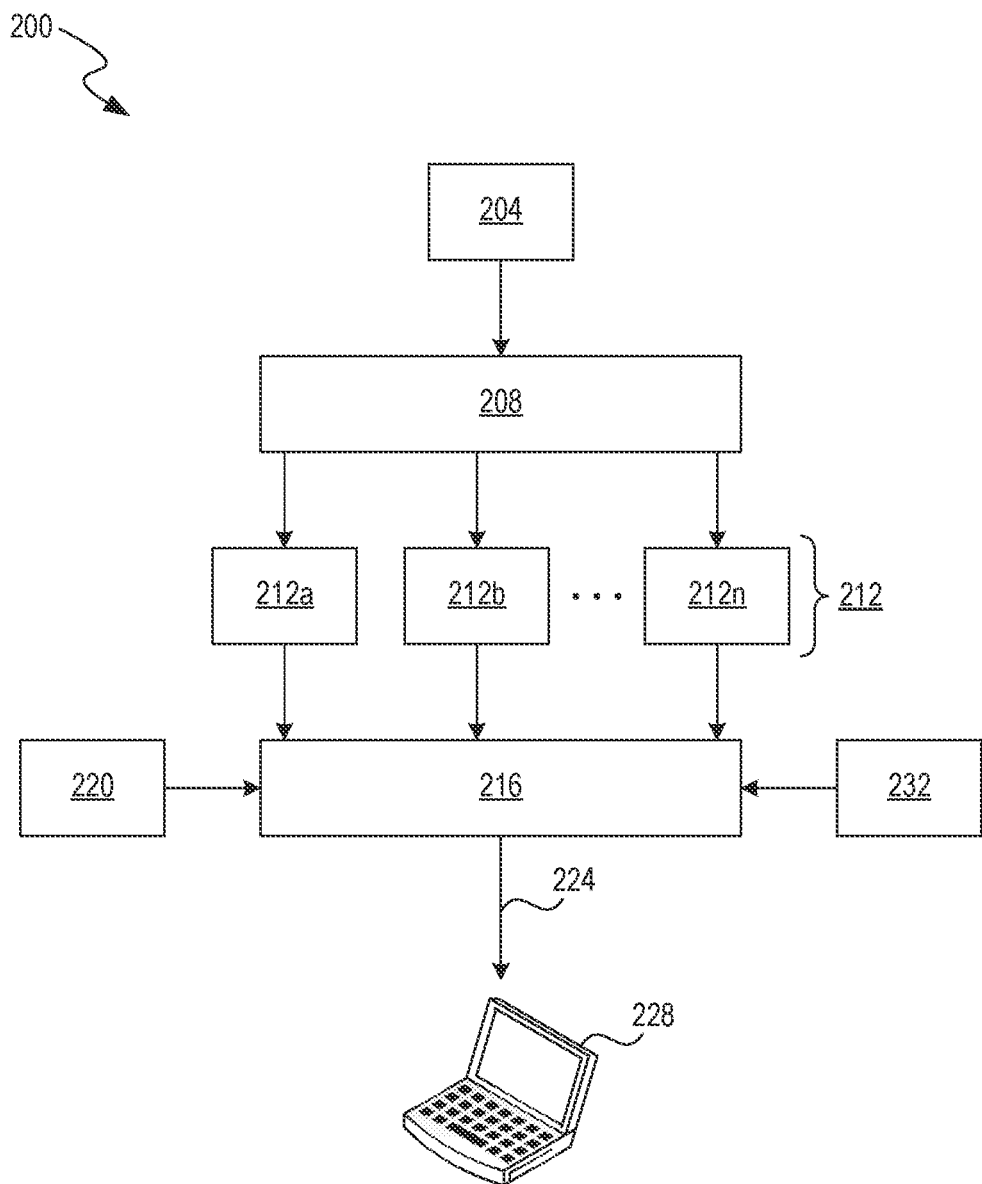
FIG. 2 is a block diagram illustrating an example machine learning (ML) system, in accordance with one or more embodiments.

FIG. 2 is a block diagram illustrating an example ML system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features $212a, 212b, \ldots, 212n$. The feature extraction module 208 reduces the redundancy in the input data 204, e.g., repetitive data values, to transform the input data 204 into the reduced set of features 212, e.g., features $212a, 212b, \ldots, 212n$. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place. The validation set 232 can include data corresponding to confirmed anatomical features, tissue states, tissue conditions, diagnoses, or combinations thereof. This allows the detected values to be validated using the validation set 232. The validation set 232 can be generated based on analysis to be performed.

Figure 3:
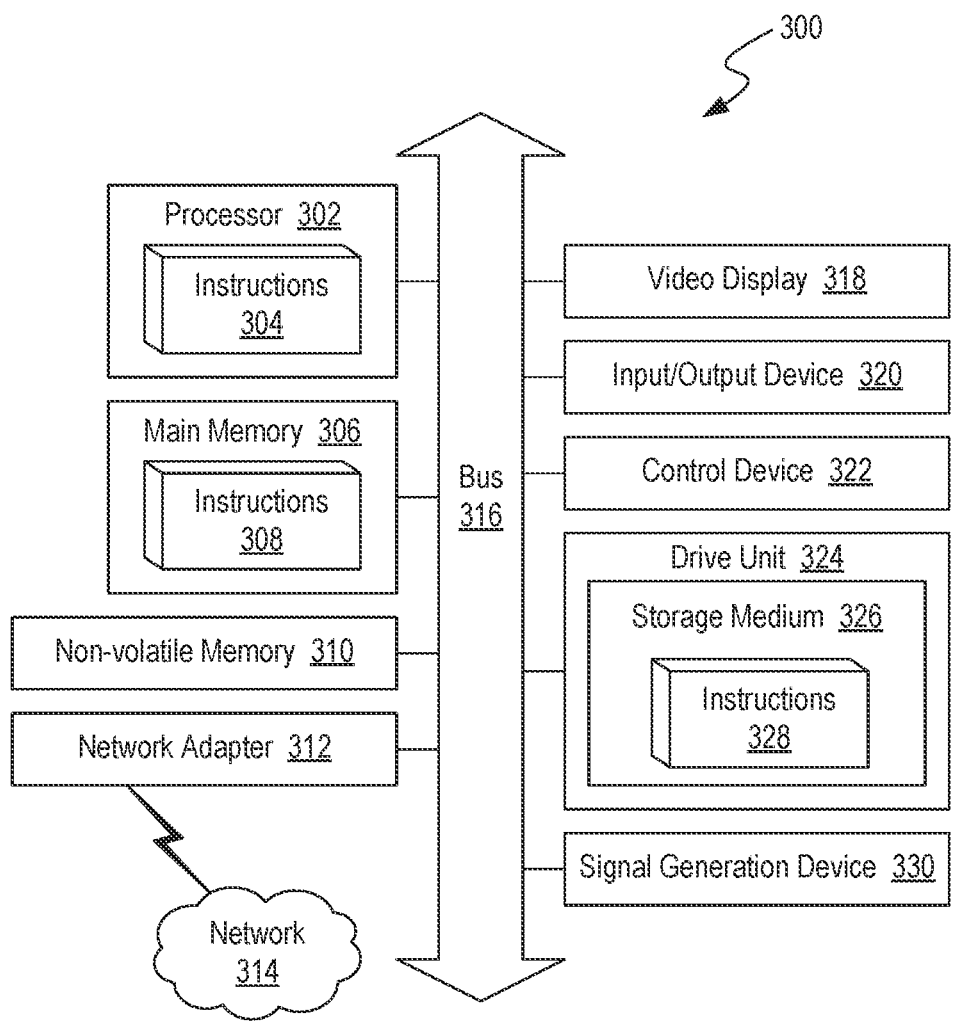
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual reality (VR)/AR systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
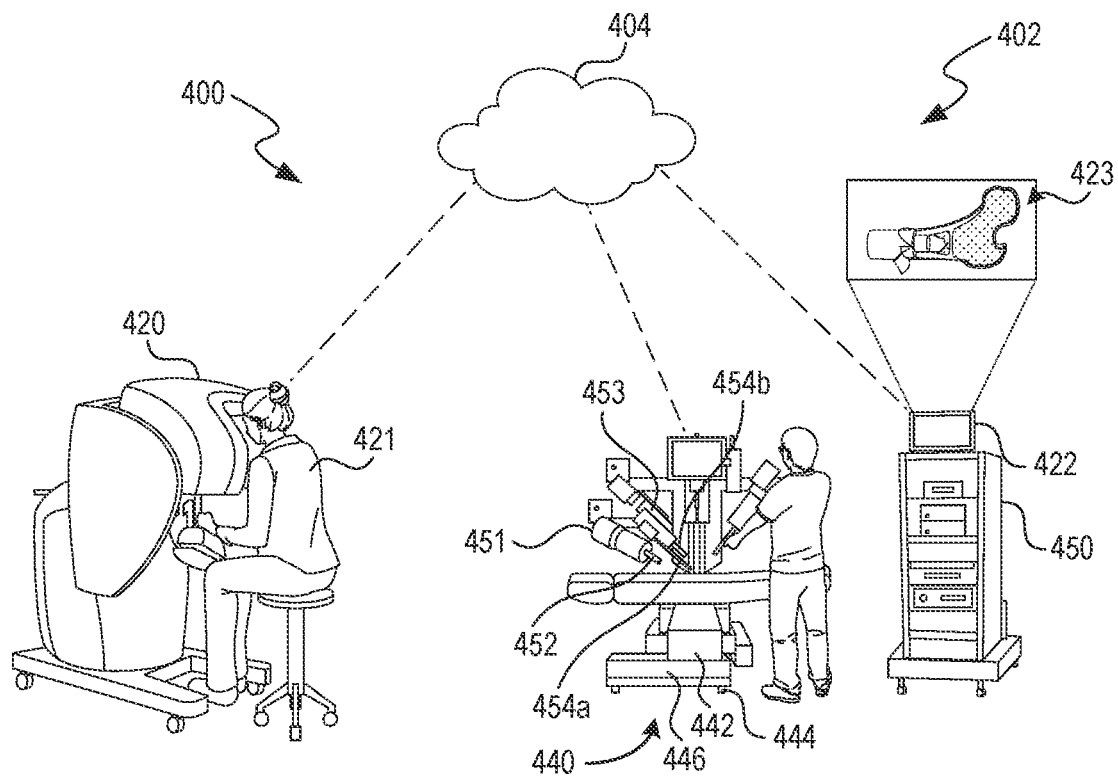
FIG. 4A is a block diagram illustrating an example robotic surgical system, in accordance with one or more embodiments.

FIG. 4A is a block diagram illustrating an example robotic surgical suite or system 400 ("robotic surgical system 400"), in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1). The robotic surgical system 400 can be configured to provide telepresence control by one or more consultants at remote locations based on a pre-operative surgical plan, inter-operative surgical event(s) at the surgical suite, etc. ML algorithms and other techniques disclosed herein can be used to manage surgical suite resources, schedule consultants, manage permission rights, and/or adjust network flow to improve surgical outcomes. For example, flow of network traffic at the surgical suite can be controlled to maintain a threshold level of control of the medical equipment by the user.

The robotic surgical system 400 includes a user device or console 420 ("console 420"), a surgical robot 440, and a computer, controller, or data system 450. The console 420 can be on-site or at a remote location and operated by a surgeon and can communicate with components in a surgical suite or an operating room 402 ("operating room 402"), remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc., or other features disclosed herein to perform surgical step(s) or procedures or implement steps of processes discussed herein.

Surgical robot 440 includes mobile unit 446. Mobile unit 446 is described in more detail with reference to FIG. 9. Mobile unit 446 can include actuators, wheels 444, and a motor 442. Mobile unit 446 includes elements enabling movement of surgical robot 440. For example, an actuator moves and controls mechanisms of surgical robot 440. An actuator is enabled by a control device (controlled by control signal), which can be an electric voltage or current, pneumatic, or hydraulic fluid pressure. Wheels 444 can be bidirectional or omnidirectional using tracks. In embodiments, mobile unit 446 includes dedicated sensors or processing abilities, and communicates with surgical robot 440 to enable coordination of robotic arms. Mobile unit 446 can receive user input data from a CAD GUI to determine movements required of surgical robot 440.

A consultant device 401 can communicate via the network 404 with components of the robotic surgical system 400, monitoring equipment, or other components of the robotic surgical system 400. The surgical robot 440, or other components disclosed herein, can communicate with and send collected data (e.g., sensor readings, instrument data, surgical robot data, etc.) to at least one database or data system 450, which are accessible to the consultant(s). This information can be used to, for example, create new ML training data sets, generate procedure plans, perform future simulations, post-operatively analyze surgical procedures, or the like. The controller or data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A mobile network test module may measure the latency of the wireless communication established between the robotic surgical system and the consultant device 401 to manage network flow. A measured/determined latency of a wireless network may be the same as a latency of a network that includes the wireless network, where the network may include a starting point/node for data to be transmitted to an ending point/node, and where the data is communicated by one computer/device associated with a surgical site to another computer/device associated with a location of the remote physician/surgeon. Scheduling of consultants can be based, at least in part, on expected latency (e.g., latency within the network 404 or other network) required to perform the telesurgery based on the received one or more surgery data. For example, a scheduling module may be configured to determine the requirement of the bandwidth (e.g., 10 MHz, 20 MHz, 30 MHz, etc.) needed and/or expected latency (e.g., ±50 milliseconds, 70 milliseconds, 100 milliseconds, etc.). The parameters for scheduling participation of the consultant device 401 can be selected by a surgical team, healthcare provider, or the like.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one or more users can observe the patient being operated on, or the product being assembled, for example. In some embodiments, the display can show images, such as, but not limited to, medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

In embodiments, the robotic surgical system 400 performs robotic joint arthroscopic procedures based on patient data to improve outcomes. For example, the robotic surgical system 400 analyzes patient joint data to identify and evaluate anatomical structures, tissue (e.g., bone, soft tissue, etc.), biomechanics, and other features of the joints. The robotic surgical system 400 can perform one or more simulations to develop a robotic-enabled surgical plan that achieves one or more targeted outcomes. Image processing can be applied to patient images (e.g., scans, video, or the like) to determine elasticity, strength, and other properties of soft tissue, such as cartilage, tendons, synovial fluid, or the like.

The robotic surgical system 400 can assign properties to structures of the joint to accurately represent the functionality of the joint. This allows simulations to accurately represent complex anatomical structures. Advantageously, the robotic-enabled surgical plan can include surgical steps that can be performed with a higher degree of accuracy than manually performed steps. Additionally, the robotic surgical system 400 can dynamically modify surgical steps based on real-time analysis of the surgical site using machine learning algorithms to improve performance. In some embodiments, the robotic-enabled surgical plan can include both autonomously performed robotic surgical steps and manual surgical steps. This allows a surgical team to participate interactively with the robotic surgical system 400.

Pre-operative simulations can use a virtual patient-specific model that matches the pre-operative anatomy to generate pre-operative surgical plans. Intraoperative data can be used to generate intraoperative virtual models for intraoperative simulations performed to modify pre-operative surgical plans. For example, continuous or periodic intraoperative imaging of a surgical site can be performed to update the virtual model. If a tissue structure is modified (e.g., cut, removed, etc.), the virtual model can be updated accordingly. One or more simulations can then be performed using the modified virtual model to assess predicted outcomes based on the current state of the surgical site. Additionally, the system 900 can determine additional imaging that may be available. For example, when internal tissues are exposed via incisions or ports, the robotic surgical system 400 can automatically image the exposed internal tissue. This allows tissue analyses to be performed using near real-time or real-time acquired data.

The robotic surgical system 400 can be incorporated into or used with technology discussed in connection with FIGS. 1-8B. For example, one or more components of the robotic surgical system 400 can be incorporated into the operating room 102 discussed in connection with FIG. 1. By way of another example, a user interface and/or imaging device of the robotic surgical system 400 can be part of interface 420 discussed in connection with FIG. 4B. Output from the robotic surgical system 400 can be transmitted to controller 450 in FIG. 5 and/or various other components disclosed herein. Accordingly, the robotic surgical system 400 can be incorporated into robotic surgery systems, or utilized to perform manual surgical procedures or to perform other procedures disclosed herein.

With continued reference to FIG. 4A, the robotic surgical system 400 can include a surgical robot 440 configured to perform robotic joint arthroscopic surgery involving the extensor retinaculum. The surgical robot 440 can include the features and components discussed in connection with FIGS. 1-8B. The surgical robot 440 can receive one or more user inputs, workflow objects, and/or data files containing surgical actions for robotic movements. The user inputs can include, without limitation, type of procedure, targeted outcome, physician notes, or other user inputs disclosed herein. The workflow objects can include surgical techniques, surgical steps, surgical processes, etc. The data files can include executable instructions for performing the techniques/processes for specific surgical tools 154. The surgical robot 440 can determine one or more end effectors and/or surgical tools for performing robotic arthroscopic surgery. The end effectors and/or surgical tools can be displayed by a user interface for selective enabling and/or disabling by the user. The data files can be generated using machine learning algorithms and/or other techniques disclosed herein. In some embodiments, the surgical robot 440 can be designed to assist a surgeon in performing a surgical operation on a patient. The surgical robot 440 can include a controller, memory, and at least one robotic arm with an end effector. Likewise, embodiments of the system of FIG. 9 can include different and/or additional components disclosed herein or can be connected in different ways.

Robotic arthroscopic surgical steps can be displayed on the user interface (e.g., interfaces of displays 401/422, interface or GUI 461) in a sequence to enable execution of the data files containing the robotic movements. The arthroscopic surgical plan can be displayed for pre-operative viewing for surgical planning and/or intraoperative viewing (i.e., while the robotic surgical system robotically operates on the patient) for monitoring the procedure. For intraoperative viewing, the robotic surgical system 400 can determine information to be displayed based on received user input while controlling one or more of the tools operated by the robotic surgical system according to the user input. For example, predicted outcomes can be adjusted based on enabling and/or disabling of a surgical tool. The robotic surgical system 400 can select and display predicted outcomes and can also display surgical steps, surgical plans, patient databases (e.g., patient databases), joint data (e.g., joint data discussed in connection with FIGS. 6B and 7-8B), or other data. For example, a patient database and associated real-time generated predicted joint movement can be simultaneously displayed while the robotic surgical system 400 controls end effectors or surgical tools 154.

The robotic surgical system 400 automatically designs a surgical workflow for and performs robotic joint arthroscopic surgery. The system of FIG. 9 includes surgical robot 440, which is a robotic system designed to perform or assist a surgeon in performing a surgical operation on a patient. In embodiments, surgical robot 440 includes a controller, a memory, and at least one robotic arm having an end effector. Likewise, embodiments of the robotic surgical system 400 can include different and/or additional components or can be connected in different ways.

In embodiments, the robotic surgical system 400 performs one or more multi-modality analyses in which one or more multi-sensing devices (e.g., multi-modality imagers, multiple imaging machines, etc.) perform (sequentially or concurrently) multiple scans/tests, such as CT scans, radiation tests, sound tests, optical tests, acoustic tests, photoacoustic tests, combinations thereof, or the like. In embodiments, a multi-modality image can simultaneously image a target region to capture images with matching perspectives relative to the target region such that features from one image can be overlayed onto another, features from multiple images can be stitched together to form a composite image, and/or cross-image features identification can be performed.

The robotic surgical system 400 can perform multimodality imaging pre-operatively, intraoperatively, and/or post-operatively. Pre-operative images can be used to generate pre-operative plans. Intraoperative images can be used to modify surgical plans, update virtual models of surgical sites, provide monitoring of the surgical procedure to a surgical team, or combinations thereof. Post-operative multiple images can be generated to evaluate the predicted outcome of the procedure, success of the procedure, or the like. In some embodiments, tests are performed during one or more scans of the target region. In a single scan test, the robotic surgical system 400 can concurrently perform multiple tests while moving along the tissue sample. In multiple scan tests, the robotic surgical system 400 sequentially performs tests during corresponding scans and/or concurrently performs multiple tests during each scan. The tests can include, without limitation, mobility tests, range of motion tests, stability tests (e.g., lateral angle stability tests), and functional tests (e.g., foot lift tests, functional hop tests, Y-balance tests, etc.), and can be performed for one or more regions of interest. The robotic surgical system 400 can generate scanning/testing protocols for specific joints based on the patient's condition. The robotic surgical system 400 can perform different testing, imaging, and/or scanning protocols based on the analysis to be performed. The robotic surgical system 400 can compare pre-operative data and post-operative data to determine prediction accuracy scores for the surgical procedure, rehabilitation protocols, or the like. In response to prediction accuracy scores falling below a threshold score, the machine learning algorithm can be retrained to increase accuracy scores. The robotic surgical system 400 can generate patient-specific rehabilitation protocols based on the post-operative condition of the patient.

The robotic surgical system 400 can generate a virtual model based on captured images and can perform surgical simulations using the virtual model to predict at least one of joint functionality, stability of the joint, or the like. In embodiments, robotic surgical system 400 determines a next step of a surgical procedure to be performed by surgical robot 440 in accordance with a surgical plan. For example, an arthroscopic surgical plan can be modified based on the surgical simulations to achieve at least one of target post-operative functionality, stability of the joint, or other characteristics of the joints. Pre-operative images can be used to perform pre-operative surgical simulations to generate an initial surgical plan. Intraoperative images can be used to perform intraoperative simulations to allow for adjustments to the surgical plan based on newly captured image data. For example, if an unplanned alteration to tissue occurs, robotic surgical system 400 can identify the alteration and perform new simulations to determine how the alteration may affect the joint. The robotic surgical system 400 generates a modified surgical plan to achieve desired post-operative outcomes.

The robotic surgical system 400 can control imaging equipment to capture images of the altered tissue to generate an alternate or modified surgical plan. In the procedures discussed herein, the robotic surgical system 400 can acquire and analyze images to determine how to robotically apply one or more sutures to anchors. Post-operative simulations (e.g., functionality simulations, stability simulations, range of motion simulations) can use a real-time three-dimensionally generated virtual model. In some procedures, the robotic surgical system 400 can identify, using image processing techniques, one or more damaged tissue structures contributing to instability of a joint. The robotic surgical system 400 can then determine locations of anchoring and tethers for compensating for the one or more damaged tissue structures so as to, for example, increase stability of the joint while maintaining a predetermined threshold joint functionality value. The predetermined threshold joint functionality value for maintaining a minimum range of motion of the joint can be inputted by the user or determined by robotic surgical system 400. Example ranges of motion of joints are discussed in connection with FIGS. 7, 8A, and 8B.

In embodiments, tests are performed during one or more scans of the target region. In a single scan test, the robotic surgical system 400 can concurrently perform multiple tests while moving along the tissue sample. In multiple scan tests, system 600 sequentially performs tests during corresponding scans and/or concurrently performs multiple tests during each scan. The robotic surgical system 400 can perform different testing, imaging, and/or scanning protocols based on the analysis to be performed.

The robotic surgical system 400 can facilitate communication with another robotic surgical system, doctor, surgeon, or other medical professional by providing results (e.g., multi-modality data, raw data, visualizations of the data, and the like) from the test(s) in real-time. Further, the robotic surgical system 400 can combine the results from imaging device(s) to provide a diagnosis of a tissue sample, target region, surgical site, or combinations thereof. In surgical procedures, the results can be automatically transmitted to a surgical robot that analyzes the results to perform one or more surgical steps. Surgical robot 440 can request additional information from the robotic surgical system 400 to, for example, complete a surgical step, confirm completion of a surgical step, plan a surgical step, plan a series of surgical steps, or the like. For example, robotic surgical system 400 can receive multi-modality results from another system to perform a multi-modality-guided robotic surgical step. In embodiments, the results are displayed via display 422 for viewing by the surgical team, as shown in FIG. 4A. Additionally, or alternatively, the results can be viewable via console 420 by user 421 of FIG. 4A while, for example, monitoring or performing one or more surgical steps.

The robotic surgical system 400 includes the surgical robot 440 for performing robotic joint arthroscopic surgery for the lateral EDL tendon portion of the anatomy. The EDL is situated at the lateral part of the front of the leg. The EDL arises from the lateral condyle of the tibia, from the upper three-quarters of the anterior surface of the body of the fibula, from the upper part of the interosseous membrane, from the deep surface of the fascia, and from the intermuscular septa between the EDL and the tibialis anterior on the medial, and the peroneal muscles on the lateral side. Between the EDL and the tibialis anterior are the upper portions of the anterior tibial vessels and deep peroneal nerve. The EDL passes under the superior and inferior extensor retinaculum of the foot in company with the fibularis tertius, and divides into four slips, which run forward on the dorsum of the foot and are inserted into the second and third phalanges of the four lesser toes. The extensor retinaculum of the arm is located on the back of the forearm, just proximal to the hand. The extensor retinaculum is continuous with the palmar carpal ligament, which is located on the anterior side of the forearm. The superior extensor retinaculum of the leg is the upper part of the extensor retinaculum of the foot, which extends from the ankle to the heelbone.

The surgical robot 440 can request additional information from the robotic surgical system 400 to, for example, complete a surgical step, confirm completion of a surgical step, plan a surgical step, plan a series of surgical steps, or the like. For example, the robotic surgical system 400 can receive multi-modality results from another system to perform a multi-modality-guided robotic surgical step. In embodiments, the results are displayed via display 422 for viewing by the surgical team, as shown in FIG. 4A. Additionally, or alternatively, the results can be viewable via console 420 by a user 421 of FIG. 4A while, for example, monitoring or performing one or more surgical steps.

The robotic surgical system 400 comprises surgical robot 440, which is a robotic system designed to assist a surgeon in performing a surgical operation on a patient. Surgical robot 440 includes a controller, memory, and at least one robotic arm with an end effector. Surgical robot 440 may further include a user interface for accepting control inputs from a user, such as a surgeon or other medical professional and a communications interface for transmitting and receiving data to and from a cloud for the purpose of training an artificial intelligence operating within the surgical robot or receiving remote commands from a remote user or an artificial intelligence existing external to the surgical robot 440. The surgical robot 440 may additionally comprise a plurality of sensors for providing feedback to the user or an artificial intelligence.

In embodiments, robotic surgical system 400 is used to simulate virtual models. Virtual models can be two-dimensional virtual models, three-dimensional models, and other models for representing anatomical features of the patient. The virtual models can have predefining kinematics, properties (e.g., tissue properties, cartilage properties, bone properties, implant properties, suture properties, anchor properties, etc.), dynamic characteristics, or the like. This allows virtual models to accurately represent pre-operative conditions of complex anatomical structures, such as joints. Pre-operative virtual models can represent predicted outcomes for joints, such as improved functionality, stability, or the like. The virtual models can be used to perform simulations to generate simulation data. In some embodiments, virtual models can incorporate or be based on 3D renderings of medical images.

A 3D rendering is a mathematical representation of an object or surface as such object or surface would appear by width, breadth, and depth dimensions. The 3D rendering that is generated transforms the medical images into high-quality, detailed, and lifelike images. The 3D rendering can be generated by robotic surgical system 400. For example, robotic surgical system 400 uses computer graphics processing to generate 3D data and models. The robotic surgical system 400 creates a lifelike or non-photorealistic image. The 3D rendering output is a digital file of an object created using software or through 3D scanning.

In embodiments, robotic surgical system 400 includes a computer-aided design (CAD) graphical user interface (GUI). The CAD GUI is a user interface for a computer software system to design surgical processes for patients. CAD refers to the use of computers to aid in the creation, modification, analysis, or optimization of a design, such as a surgical procedure. CAD software is used to increase the productivity of the designer or user, such as a doctor or medical professional, to improve the quality of design, to improve communications through documentation, and to create a database for the procedure. CAD output is often in the form of electronic files for print, machining, or other manufacturing operations.

The GUI, or graphical user interface, is an interface(s) that may either accept inputs from users, provide outputs to users, or perform both actions. In one case, a user can interact with the interface(s) using one or more user-interactive objects and devices. The user-interactive objects and devices may include user input buttons, switches, knobs, levers, keys, trackballs, touchpads, cameras, microphones, motion sensors, heat sensors, inertial sensors, touch sensors, or a combination of the above. Further, the interface(s) may be implemented as a command line interface (CLI), a GUI, a voice interface, or a web-based user interface.

The CAD GUI enables a user, such as a surgeon, doctor, medical professional, etc., to view an area of a patient's body that requires surgery in a 3D space. The CAD GUI also allows the user to select various surgical tools 154, materials, and techniques required for the surgery and allows the user to manipulate the surgical tools 154, materials, and techniques, as rendered over the patient's 3D image to perform the processes and steps needed for the surgery in a virtual space. The user's movements and actions may be saved and stored in an operation database to assist the surgeon in performing the surgery or to provide the surgical robot 440 with the approximate (x, y, z) coordinates to perform the surgery. The (x, y, z) coordinates of the anatomy specify the position of any anatomical structure in three-dimensional space using distances to three mutually perpendicular planes (or, equivalently, by a perpendicular projection onto three mutually perpendicular lines). In embodiments, n Cartesian coordinates (an element of real n-space) specify the structure in an n-dimensional Euclidean space for any dimension n.

The CAD GUI allows other users to view or replay the surgery in the 3D space to alter or adjust movements or actions to perform the surgery. In some embodiments, the CAD GUI may provide the user or surgical robot 440 with a list of materials needed, a list of surgical tools 154 required, a workflow process of the surgical procedure, a 3D visual replay of the surgical procedure, etc. A hospital network provides medical information of a patient to the surgical robot network, such as electronic health records, medical images (MRIs, X-rays, etc.), a list of the patient's doctors and health care professionals, the patient's current medications and prescriptions, the patient's medical history, the names of the patient's specialists, etc.

A GUI or guided user interface may be an interface(s) may either accept inputs from users or provide outputs to the users or may perform both the actions. In one case, a user can interact with the interface(s) using one or more user-interactive objects and devices. The user-interactive objects and devices may comprise user input buttons, switches, knobs, levers, keys, trackballs, touchpads, cameras, microphones, motion sensors, heat sensors, inertial sensors, touch sensors, or a combination of the above. Further, the interface(s) may either be implemented as a Command Line Interface (CLI), a Graphical User Interface (GUI), a voice interface, or a web-based user-interface. The CAD GUI 946 allows a user, such as a surgeon, doctor, medical professional, etc., to view an area of a patient's body that requires surgery in a 3D space. The CAD GUI 946 also allows the user to select various surgical tools 154, materials, and techniques, that required for the surgery and allows the user to manipulate the surgical tools 154, materials, and techniques, rendered over a patient's 3D image to perform the processes and steps needed for the surgery in a virtual space.

In embodiments, one or more machine learning (ML) systems trained to correlate feature vectors to prior patient data having favorable outcomes are executed. For example, surgical robot 440 includes one or more ML systems trained to correlate feature vectors to expected outputs in the training data. As part of the training of an ML model, the ML system can form a training set of favorable outcomes (e.g., prior patient data with favorable outcomes) and training labels by identifying a positive training set of features that have been determined to have a desired property in question, and, in some embodiments, forms a negative training set of features that lack the property in question. The property in question can include, without limitation, one or more threshold outcomes/scores, therapeutic effect(s), or other criteria selected by, for example, a user or surgical team.

The surgical robot 440 can include a correlation module configured to retrieve data from a surgery database based on the surgery type. The correlation module performs correlations on selected parameter(s) to determine if parameters are highly correlated. The correlation module determines if the correlation coefficient is over the predetermined threshold, for example, over a correlation coefficient (e.g., a predetermined correlation coefficient). If it is determined that the correlation coefficient is over the predetermined threshold, then the correlation module extracts the best match data point from the data set. The correlation module then stores the data entry for the best match data point in a recommendation database. If it is determined that the correlation coefficient is not over the predetermined threshold, or after the data entry for the best match data point is stored in the recommendation database, the correlation module determines if there are more parameters remaining in the surgery database. If it is determined that there are more parameters remaining in the surgery database, the correlation module selects the next parameter in the surgery database and the process returns to performing correlations on the parameters. If it is determined that there are no more parameters remaining in the surgery database, the correlation module returns to the base module.

The recommendation module begins operation by being initiated by the base module, e.g., using a message, a software or hardware trigger, an interrupt, or another signal. The recommendation module filters the recommendation database based on the correlation coefficient (e.g., the highest correlation coefficient). The recommendation module selects the highest correlated data entry in the recommendation database. Other techniques can be used.

For arthroscopic procedures, the training data can include, without limitation, pre-operative data, post-operative data, outcomes (e.g., short-term outcomes, long-term outcomes, etc.), and surgical data (e.g., adverse events, physician input, etc.). For leg-related procedures, the training data can include threshold criteria (e.g., threshold values, threshold scores, etc.), scores (e.g., American Orthopedic Foot and Ankle Society (AOFAS) score, Visual Analogue Scale (VAS) score, Cumberland Ankle Instability Tool (CAIT) scores, quality of life scores, pain scores, etc.), stress radiographs to measure tilt test (e.g., talar tilt test) and anterior drawer tests, or the like. The threshold criteria can be selected as a favorable outcome. The values/scores can be selected as threshold outcomes or therapeutic effect(s) for approving surgical plans, simulations, etc. For arm-related procedures, the training data can include, without limitation, thresholding values/scores, Disabilities of the Arm, Shoulder, and Hand (DASH) questionnaire scores, etc. The surgical robot 440 can set up and train the ML model as discussed in connection with FIG. 2 and can include one or more ML systems (e.g., ML system 200 of FIG. 2).

The surgical robot 440 can also generate surgical procedures or plans with joint stabilization predictions (e.g., post-operative stability scores of joints, long-term stability scores of joints, etc.), joint mechanics predictions (e.g., one or more target characteristics of joint mechanics), predicted restored function of the joint, combinations thereof, or the like. The surgical robot 440 can manage pain by, for example, determining ligament-attachment joint stabilization steps for utilizing connectors to adjust movement of the joint. For example, robotic surgical system 400 can identify attachment sites to be physically connected to other structures (e.g., ligaments, bones, muscle, etc.) of the joints.

In some implementations, robotic surgical system 400 can identify one or more attachment points along an anatomical structure (e.g., extensor retinaculum, dorsal carpal ligament, posterior annular ligament, antebrachial fascia, etc.) that are capable of serving as attachment points for limiting motion of the joint, reinforcing the joint, limiting range of motion of the joint, combinations thereof, or the like. Images of the anatomical structure can be analyzed to determine the contribution of the anatomical structure to properties of the joint. The robotic surgical system 400 can then identify the number and position of attachment points based on the desired forces to be applied to the anatomical structures. The properties of implantable connectors can be selected based on target outcomes. For example, unextendible, flexible sutures can connect a ligament to a bone on the opposite side of a joint to limit or fix a range of motion of a joint. This can allow the joint to have normal range of motion in one direction while limiting the range of motion in an opposite direction.

The surgical robot 440 can use one or more ML systems to analyze real-time data (e.g., video, images, etc.) of a surgery site to determine one or more candidate surgical steps, generate predicted outcomes for candidate surgical steps, and/or generate simulations for physician review. As shown in FIG. 4C, a physician can view a surgical site 465 annotated with, for example, labeled structures of a joint, joint mechanics information, plan surgical steps, surgical tools, or the like.

In embodiments, robotic surgical system 400 analyzes patient joint data to evaluate at least one of anatomical structures, tissue, or biomechanics of joints of the patient. A simulation is performed to generate a surgical plan, wherein the surgical plan is intended to achieve a targeted outcome for the surgical procedure. For example, patient data 472 includes, without limitation, target sites (e.g., attachment sites, anchor sites), joint data, mobility data, and other patient data related to the surgical procedure. Example information for display is discussed in connection with FIGS. 6A, 6B, 7, 8A, and 8B. The robotic surgical system 400 can predict post-operative outcomes based on, for example, properties of ligaments, properties of implantable connectors, etc. to improve joint stabilization, limit disease progression, and/or improve patient biomechanics. The predicted post-operative outcomes can be for a selected time or period of time. For example, robotic surgical system 400 can predict post-operative outcomes one month after surgery, six months after surgery, one year after surgery, two years after surgery, or the like. Age-related changes to anatomical structures, tissue, and other anatomical elements can be used to generate the predicted time-varying post-operative outcomes. By way of example, soft tissue, such as ligaments, may become hardened or lose elasticity over a period of time. The robotic surgical system 400 can predict biomechanics at joints based on such tissue changes. This allows a user to evaluate long-term outcomes of surgical procedures based on typical age-related effects.

In embodiments, patient joint data comprises patient images. Analyzing the patient joint data comprises applying image processing to the patient images to determine elasticity or strength of at least one of cartilage, tendons, or synovial fluid of the patient. For example, robotic surgical system 400 generates post-operative outcomes based on different types of simulations. The simulations can include non-linear characteristics (e.g., micromechanics, mechanical behavior, etc.) of soft tissue. Linear, non-linear, and other mechanical properties can be applied to tissue to generate linear finite element models, non-linear finite element models, joint modeling (e.g., linear joint modeling, non-linear joint modeling, dynamic joint modeling, etc.), or the like. For example, the robotic surgical system 400 can model and simulate the dynamic behavior of non-linear anatomical structures of a joint. The dominant characteristics of the joints can be identified and used to determine anatomical features to be modified.

In embodiments, robotic surgical system 400 includes an imaging device, which is any device capable of collecting data which can be used to create an image, or a representation of a physical structure or phenomena. In embodiments, a plurality of surgical tools comprise an imaging sensor. The terms imaging device and imaging sensor are used interchangeably herein. The imaging device can include any device capable of detecting sound or electromagnetic waves and assembling a visual representation of the detected waves. Imaging devices can collect waves from any part of the electromagnetic spectrum or sounds at any range of frequencies, often as a matrix of independently acquired measurements that each represent a pixel of a 2D or 3D image. These measurements may be taken simultaneously or in series via a scanning process or a combination of methods. Some pixels of an image produced by an imaging device may be interpolated from direct measurements representing adjacent pixels in order to increase the resolution of a generated image.

The imaging device can include an algorithm or software module capable of determining qualitative or quantitative data from medical images. The algorithm can be a deep learning algorithm trained on a data set of medical images. The imaging device may further refer to a device used to acquire medical imagery by any means including MRI, CT, or X-ray. The imaging device may further refer to a device used to acquire medical imagery by PET, ultrasound, or arthrography. The imaging device may further refer to a device used to acquire medical imagery by angiography, fluoroscopy, or myelography.

The imaging device can be controlled to acquire images that can be annotated with, for example, patient information, procedure information, or the like. The patient information can include, without limitation, damaged structures of the joint, joint mechanics information (e.g., a range of motion, degrees of freedom, areas contributing to joint instability, motion of FIGS. 7-8B, etc.), ligaments, bone, soft tissue, muscle, synovial sacs, or the like. The procedure information can include, for example, completed surgical steps, planned future surgical steps, information (e.g., calculations, technique information, etc.), attachment sites (e.g., anchor sites, suture sites, etc.), connector information (e.g., number of connectors, dimensions of connectors, properties of connectors, orientation of connectors, routing of connectors, etc.), and other information discussed in connection with FIGS. 1-8B, and other information disclosed herein.

The imaging device refers to any device capable of collecting data which can be used to create an image, or a representation of a physical structure or phenomena. An imaging device may include any device capable of detecting sound or electromagnetic waves and assembling a visual representation of the detected waves. The imaging device may collect waves from any part of the electromagnetic spectrum or sounds at any range of frequencies, often as a matrix of independently acquired measurements which each representing a pixel of a two or three-dimensional image. These measurements may be taken simultaneously or in series via a scanning process or a combination of methods. Some pixels of an image produced by an imaging device can be interpolated from direct measurements representing adjacent pixels in order to increase the resolution of a generated image.

In embodiments, a surgery is designed to address ankle instability to, for example, improve an outcome score, such as the AOFAS score, VAS score, overall joint score, composite joint score (e.g., composite score based on weighted AOFAS and VAS scores), etc. For example, the ankle can be pre-operatively and/or post-operatively evaluated to generate both pre-operative scores (e.g., AOFAS scores, VAS scores, etc.), and/or post-operative scores. Scores can be used to evaluate the ankles, subtalar, talonavicular, and calcaneocuboid joints, as well as arthrodesis, fractures, arthroplasty, and instabilities. The wrists, hands, shoulders, knee, and other anatomical structures can be scored using different scoring protocols.

In embodiments, robotic surgical system 400 determines that a surgical step is complete based on a surgical plan. For example, the surgical plan is generated to achieve a threshold score, increase/decrease a pre-operative score(s) (e.g., threshold increase/decrease of AOFAS score, VAS score, respectively), etc. The Brostrom-Gould repair surgery is primarily used to repair the anterior talofibular ligament (ATFL) in the ankle. The recovery time for the procedure varies according to the patient but usually takes a minimum of 3-6 months. The surgery stabilizes the ankle, improves the ankle's mechanics, and restores function. The surgery helps a patient to experience less pain related to his or her injury and ankle sprains, as well as to avoid early arthrosis.

Figure 4B:
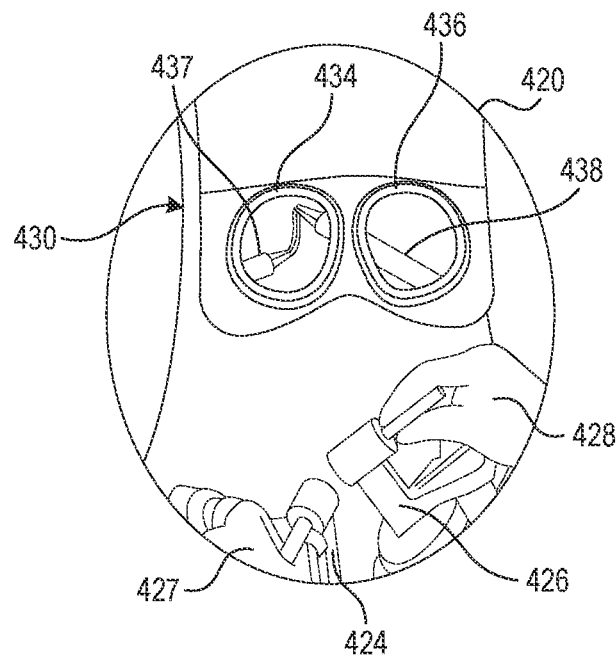
FIG. 4B illustrates an example console of the robotic surgical system of FIG. 4A, in accordance with one or more embodiments.
Figure 4C:
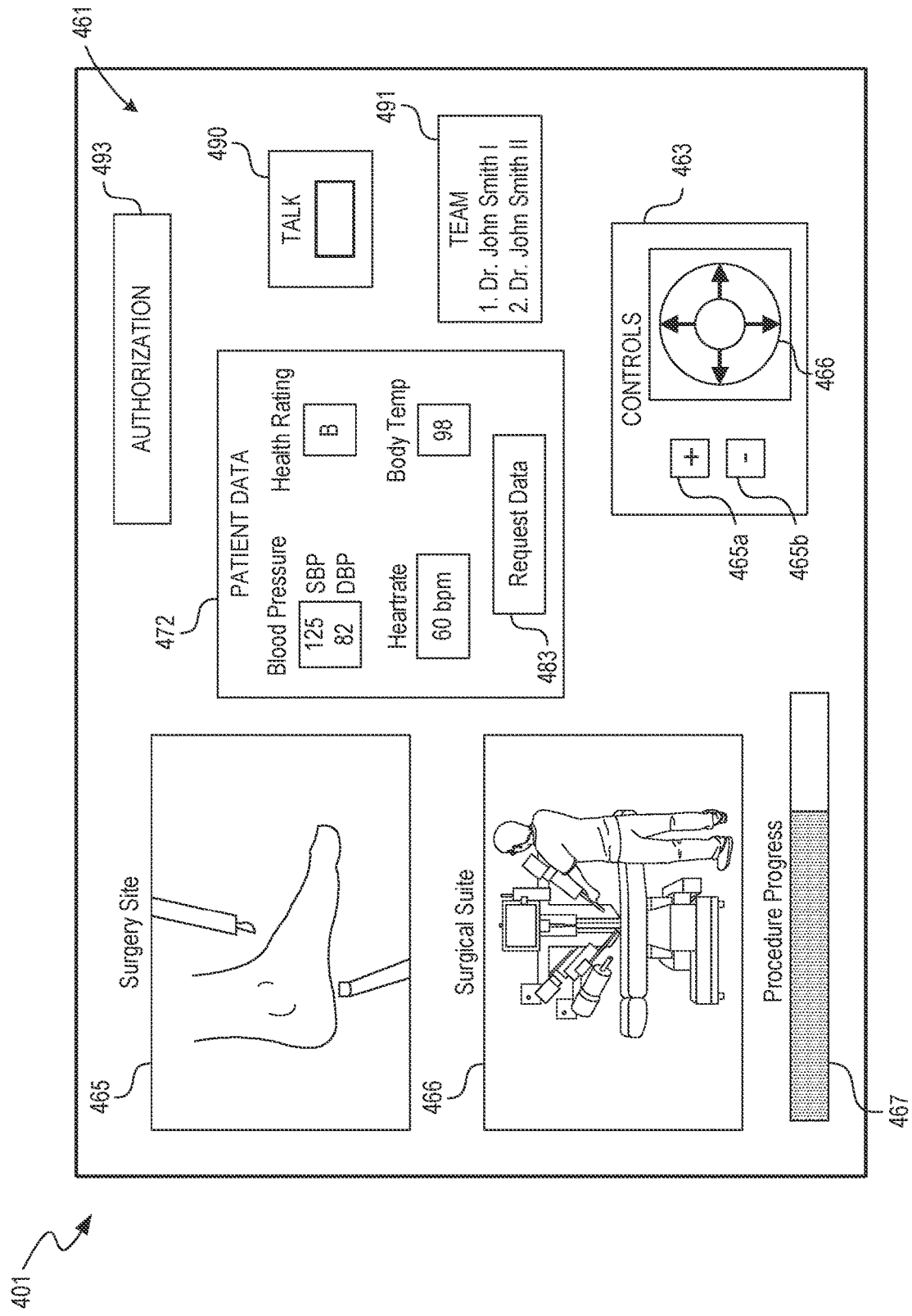
FIG. 4C illustrates an example display of a user device, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including multiwavelength images, image modality information, fused data sets, tissue types, mapped images (e.g., tissue types maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452. The surgical robot 440 can include a multi-modality imager 453 having imaging devices 454a, 454b (collectively "imaging devices 454"). The imaging devices 454 can be, for example, PET scanners, ultrasound imagers, MRI imagers, CT scanners, cameras (e.g., camera imager hardware, digital cameras, etc.), infrared imagers, etc. In embodiments, the surgical robot 440 retrieves/receives images from stand-alone X-ray machines, MRI machines, CT scanners, etc. Example imaging devices and imaging modalities are discussed in connection with FIGS. 1, 4A, and 6. The number, imaging capabilities, and configurations of the imaging devices 454 can be selected based on the imaging to be performed.

The robotic surgical system 400 can automatically generate multi-modality images based on surgical plans and then perform one or more surgical steps of a planned surgical procedure. In embodiments, the robotic surgical system 400 analyzes a surgical plan for a patient to generate an imaging plan for obtaining patient information for diagnostic purposes, modifying the surgical plan, performing surgical steps (e.g., one surgical step, multiple surgical steps, all surgical steps), etc. The imaging plan can include, without limitation, one or more regions of interest, targeted information, predicted features of interest, information for diagnostic purposes, or the like. The robotic surgical system 400 can generate the imaging plan based on imaging capabilities of the multi-modality imager 453. The robotic surgical system 400 can notify the surgical team to add or replace imaging devices 454 to achieve the desired imaging capability.

The robotic surgical system 400 can retrieve available images of a patient from, for example, electronic medical records, image databases, and/or other imaging sources. The robotic surgical system 400 can identify and retrieve images that can be processed for producing one or more multi-modality images. The robotic surgical system 400 can determine whether additional unavailable images could be useful for generating multi-modality images that (1) meet at least one threshold criteria (e.g., a confidence score), (2) identify features of interest, (3) have diagnostic capability criteria, etc. In some procedures, the robotic surgical system 400 retrieves available images and determines imaging programs or parameters (e.g., positions, imaging settings, etc.) of one or more of the imaging devices 454 corresponding to the available images. In embodiments, an ML system (see FIG. 2) can be used to generate imaging plans based on training sets. The training sets can include, for example, single modality training sets, composite multi-modality training sets, confirmed diagnostic training sets, and other training sets. This allows the robotic surgical system 400 to perform re-training procedures for continuously or periodically training the ML system. Newly captured images can be keyed to or matched with the retrieved images, thereby increasing accuracy of the multi-modality images. During intro-operative imaging, the images can be analyzed in real-time to further control the robotic surgical system 400.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds. The adverse surgical events can be identified using an ML model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with robotic links, motors, and integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein. As shown by FIG. 4A, the display 422 can display, for example, a diagnosis of tissue, images, maps, surgical plans, etc. For example, the display 422 can display a diagnostic image or map showing, for example, a bone in image 423 (discussed in more detail below with reference to multi-modality imaging), regions of interest (e.g., zones of diseased tissue, regions of tissue with specific characteristic(s), margins, etc.), features of interest, anatomical elements (e.g., cartilage, soft tissue, etc.), or the like. An example image is discussed in connection with FIG. 5. In some embodiments, a diagnostic image can include tissue density, tissue state, identified disease tissue, or the like. The system 402 can use the displayed data to perform one or more surgical steps. A user can view the display 422 to confirm the position of the tissue during the procedure.

Referring to FIGS. 4A and 4C, the consultant device 401 can display procedure information from the surgery room, equipment controls, and other data disclosed herein. Referring now to FIG. 4C, the consultant device can display a graphical user interface (GUI) 461 for telepresence consulting. The GUI 461 includes an authorization input 493 for authorizing the consultant for participation in a surgical procedure and displays procedure and patient data 465, 466, 472, 491. Imaging equipment can automatically capture images for surgical side viewing via a display 465. The GUI 461 includes a procedure progress 467 that can be updated to show completed progress for the procedure, and controls 463 can be used to operate machines/applications. The user can customize the GUI 461 by rearranging the displayed items for convenience.

The consultant can use an authorization input 493 to, for example, input user authorization information (e.g., access codes, pins, etc.), employee credential information, surgical procedure information (e.g., serial number or code for the surgical procedure), or the like to access and operate equipment. If the consultant needs additional permission rights, the consultant can request the additional permission rights using the authorization input 493. For example, if an adverse event occurs during the procedure requiring the consultant to provide additional care, the consultant can request access to the additional equipment (e.g., robotic arms of surgical robot, breathing machine, heart rate monitor, etc.) via the authorization input 493. The surgical suite system can receive the requested authorization and perform an authorization protocol routine to determine whether the consultant should be granted permission rights to the additionally requested equipment. The surgical suite system can analyze the surgical plan, planned permission rights (e.g., plan of permission rights assigning permission rights to features or steps of the surgical plan), consultant credentials and/or expertise, and/or other information disclosed herein to determine whether to grant permissions. If requested permission rights are denied, the on-site medical team can be notified of the denied request and consultant input, recommendation, etc. If the request is granted, the system can automatically establish communication and control channels for displaying the additional information for the additional equipment via the consultant device 401. The procedure progress 467 can show completed progress for the modified procedure based on the additional equipment.

Dynamic updating of the equipment controls 463 on the consultant device 401 allows the user to acquire control of additional medical equipment in the same consulting session without disrupting communication channels. This reduces the risk of latency and/or network problems that could affect the medical procedure. The controls 463 can be configured to perform all or some of the controls as discussed in connection with FIG. 4B. For example, the controls 463 can include a touch input control module 466 with input features 465a, 465b that can be used to increase or decrease, respectively, settings of equipment. The touch input control module 466 can be used to control movement of, for example, robotic surgical arms, robotic manipulators, and effectors, or the like. For example, the touch input control module 466 can be configured to provide the same controllability as the hand-operated input devices 424, 426 of FIG. 4B. In some embodiments, the controls 463 of FIG. 4C can be modified to include controls for the additional equipment such that the consultant has access to controls for operating newly available equipment in real-time while continuing to view real-time patient data 472. Data collected by and/or associated with additional equipment can automatically be added to the patient data 472.

The consultant device 401 can include a procedure viewer 465, a surgical suite or room viewer 466, and/or other viewers or windows for providing viewing (e.g., real-time or near real-time viewing) of the surgical suite (e.g., viewing at operating rooms, recovery rooms, etc.), medical team, medical equipment, etc. The consultant device 401 can display patient data 472 that can include, for example, blood pressure, health rating, heart rate, body temperature, vitals, physician notes, and/or additional patient data useful to the consultant. To change or receive additional patient data, the consultant can use a request data button 483 to send a message or notification to the on-site surgical team to provide additional patient data. The consultant can use a talk feature 490 to verbally communicate with the surgical team. The consultant device 401 can also display the surgical team information 491. The surgical team information can list physicians, nurses, staff, consultants, and other staffing information.

The robotic surgical system 400, illustrated and described in more detail with reference to FIG. 4A, can further include multiple consultant devices 401 so that multiple members of a surgical team or consultants can view the surgical procedure. The number and configuration of the consultant devices 401 can be selected based on the configuration and number of surgical robots, monitoring equipment, etc. The consultant device 401 can also display procedure data, including a surgical plan (e.g., a surgical plan including completed and future planned surgical steps), patient monitor readings, surgical suite or room information (e.g., available team members, available surgical equipment, surgical robot status, or the like), images (e.g., pre-operative images, images from simulations, real-time images, instructional images, etc.), and other surgical assist information. In some embodiments, the consultant device 401 can be an AR/VR headset, display, or the like.

Referring to FIG. 4A, the robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, California. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through artificial intelligence mapping. The software for artificial intelligence is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system. In some embodiments, the system determines the location, number, angle, and depth of arthroscopic ports (e.g., tubes, rods, etc.) to place in a patient. The system can select the location, number, angle, and depth of the arthroscopic ports based on the maneuverability of the surgical robot, maneuverability of the end effectors of the surgical robot and/or the availability of the surgical tool to place the arthroscopic ports in the patient.

Figure 5:
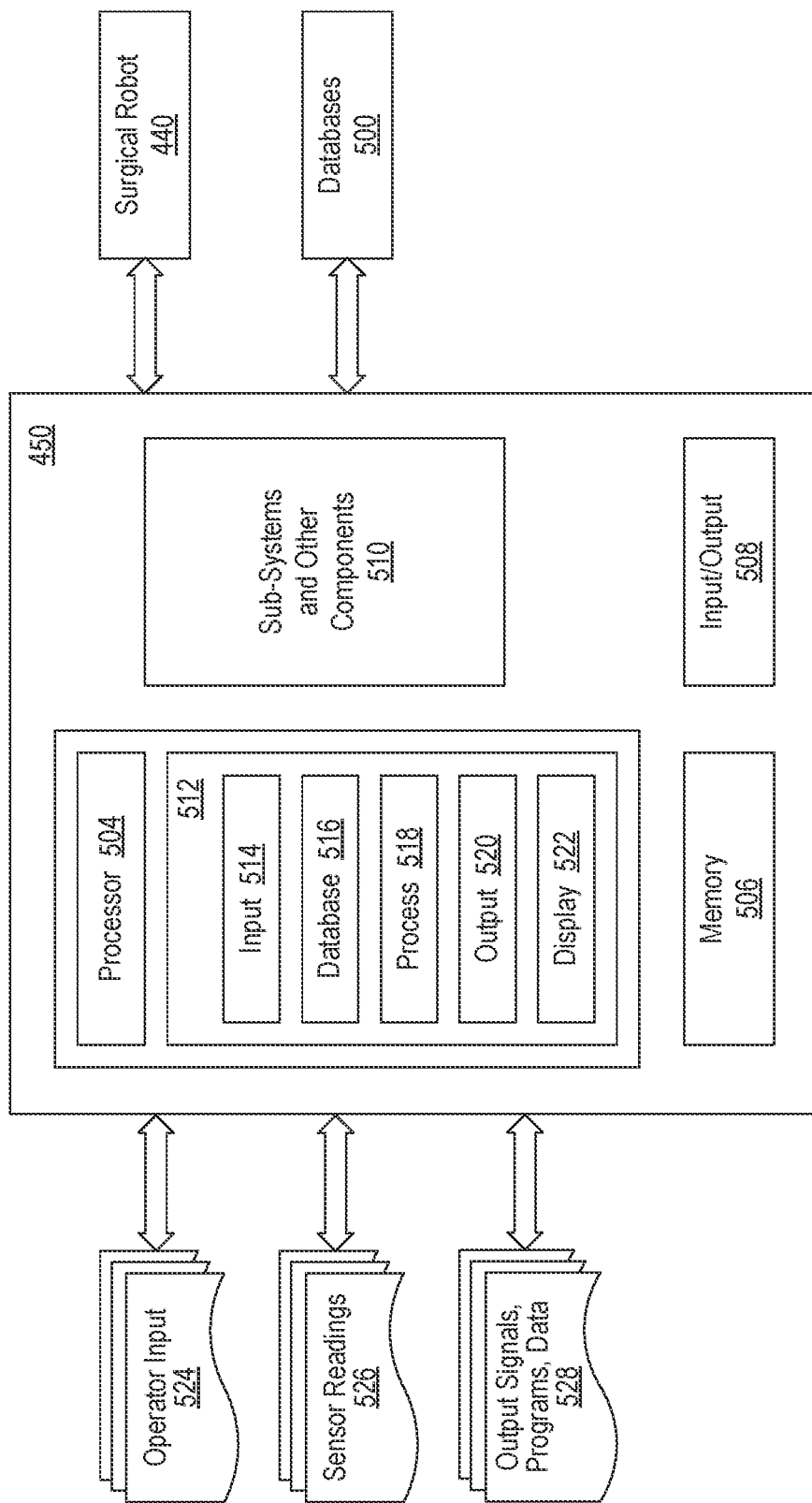
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The controller or data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices (including consultant devices), and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 500. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A network adapter 501 can be an operator authorizing device to manage communications and operation of components, as described with reference to FIG. 3. The network adapter 501 can govern and/or manage permissions to access proxy data in a computer network, track varying levels of trust between different machines and/or applications, and manage control access to surgical equipment, communications between remote devices and the surgical room, etc.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to the patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6A:
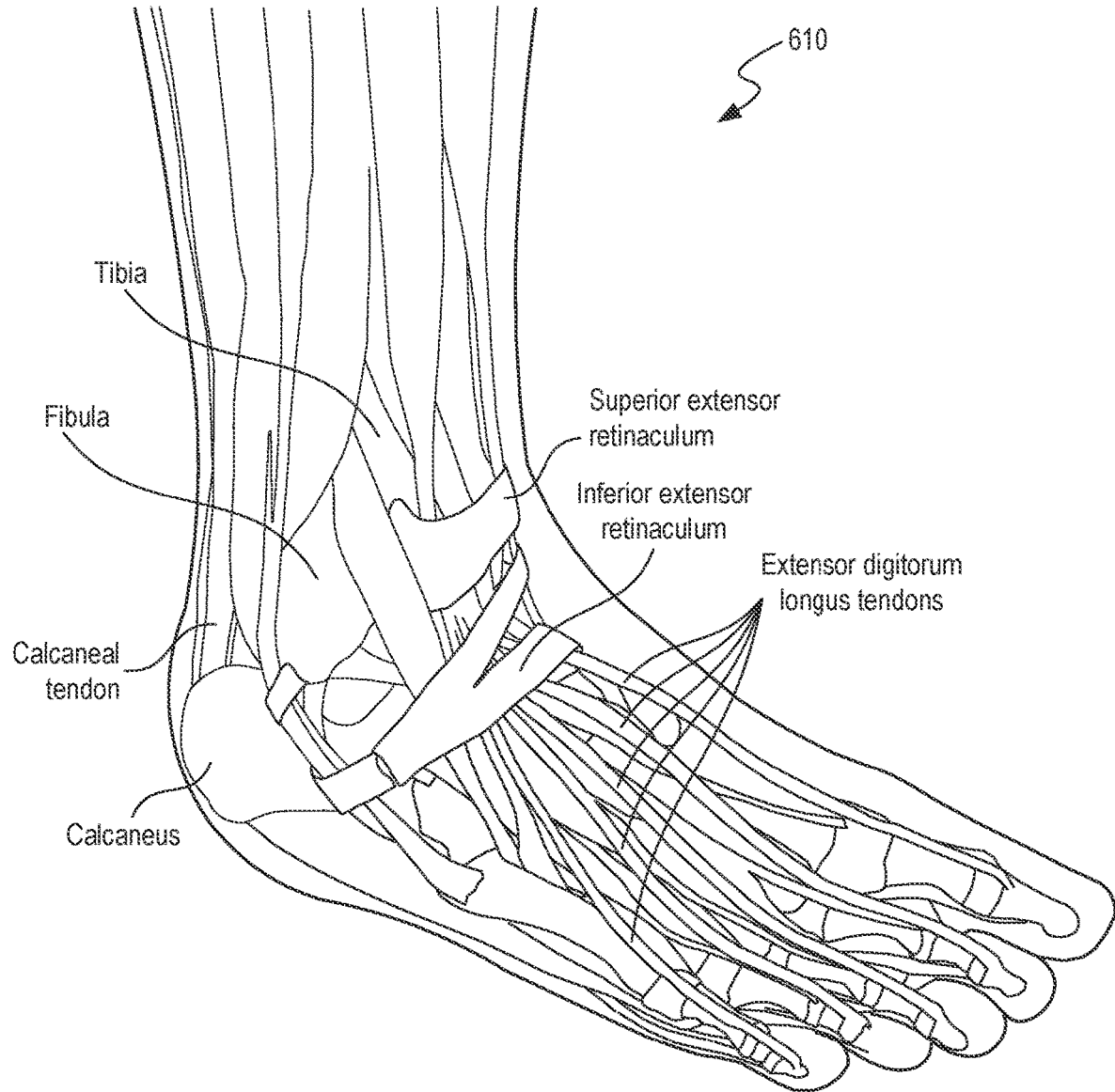
FIG. 6A illustrates an example multi-modality image of a target region, in accordance with one or more embodiments.
Figure 6B:
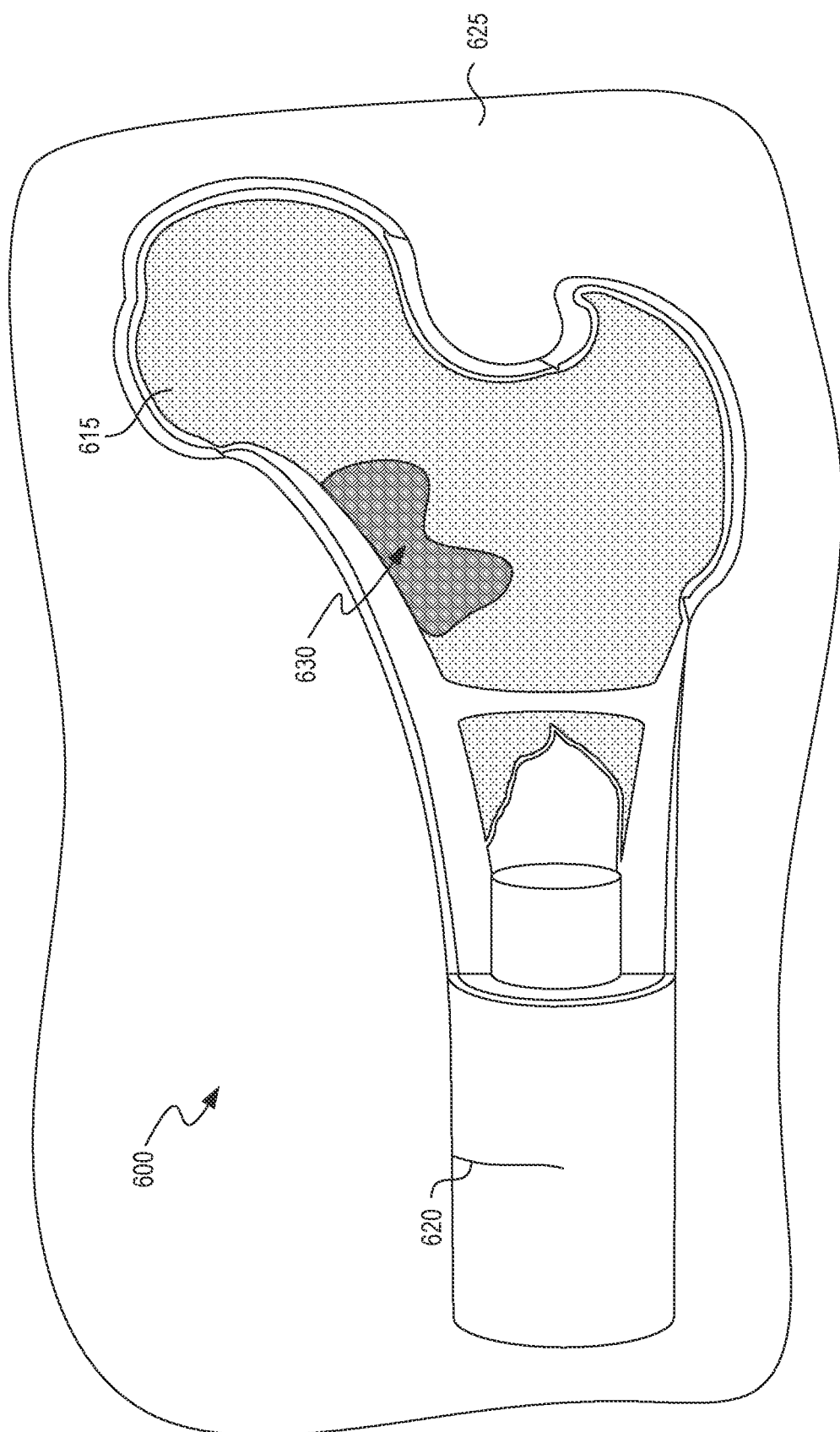
FIG. 6B illustrates an example image of another target region, in accordance with one or more embodiments.

FIG. 6A illustrates an example multi-modality image 600 of a target region, in accordance with one or more embodiments. FIG. 6B illustrates an example of another image 610, in accordance with one or more embodiments. The images 600, 610 can allow a healthcare worker to view a target region 625 to analyze an automated diagnosis, anatomical features, identify tissue of interest, etc. Systems disclosed herein can analyze a surgical plan to identify potential one or more anatomical features of interest. The system can select imaging modalities based on the potential one or more anatomical features of interest and available imaging modalities. The system can obtain at least one image for each imaging modality and generate a multi-modality image based on each of the obtained images. The system can determine one or more imaging characteristics for each potential anatomical feature of interest and correlate imaging characteristics to identify the available imaging modalities used to select the image modalities. The system can identify anatomical features in the image 600 (e.g., a pre-operative image, real-time intraoperative image, etc.). The multi-modality images 600, 610 can be generated based on a surgical plan, physician input, or other input data, and can indicate features (e.g., anatomical elements), margins, tissue type, etc.

Referring to FIG. 6A, to generate the image 600, systems disclosed herein can receive a tissue density image from an MRI device, a bone fracture image from a CT scanner, a bone degeneration or cancerous tissue image from an ultrasound machine, or images from other imagers disclosed herein. In embodiments, the image 600 is generated for a surgical plan for treating a damaged bone and can include, for example, tissue density data 615 (e.g., healthy tissue data from an MRI device), a bone fracture 620 (e.g., identified using a CT scan), diseased tissue 630 (e.g., low-density tissue, cancerous tissue, etc., from ultrasound images), or the like. The system can combine the data to generate the image 600 with features and/or information of interest. In some embodiments, the image 600 highlights regions 625 of a tissue sample according to the diagnoses and/or the values from a multi-modality device or multiple imaging devices. For example, the image 600 can annotate highlight and/or otherwise identify/emphasize features of interest. The emphasis can help direct the doctor's review of the target region 625 and/or further analysis of the patient. In embodiments, images are generated that include raw data and multi-modality images (e.g., composite images, a multilayer overlaid image, etc.) to allow a physician to perform an independent diagnosis. In embodiments, the raw data is indicated via differences in shading, color, fill patterns, express indications, display tables, selectable displays, and/ or in any other suitable manner. Similar processes can be used to generate the image 610.

The multi-modality images 600, 610 of FIGS. 6A and 6B can include selectable layers. For example, the multi-modality images can include a first layer created using a first modality, a second layer created using a second modality, and a third layer created using a third modality. A composite layer can include selected data from one or more of the three layers. The number of layers, number of imaging modalities, types of imaging modalities, data sets, fused data sets, and/or image processing (e.g., scaling of images, filtering of images, etc.) can be selected based on target characteristics of the composite layer, surgical plan (e.g., features of interest, anatomical elements, etc.). For example, the image 600 of FIG. 6 can include selectable layers each with one or more anatomical features identified (e.g., via annotation, false colors, etc.).

Figure 7:
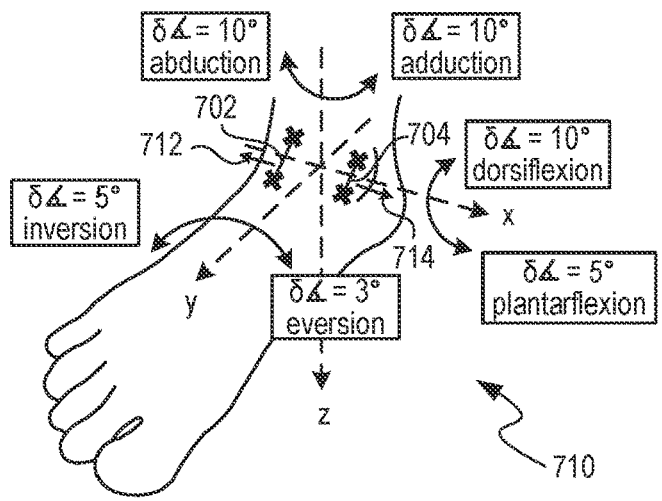
FIG. 7 shows movement of the human ankle, in accordance with one or more embodiments.
Figure 8A:
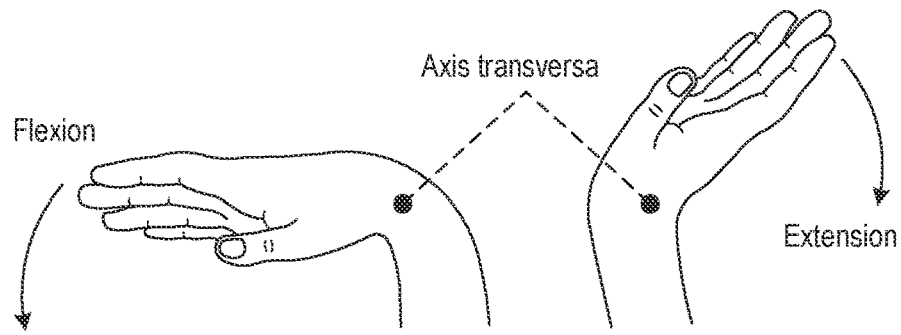
FIGS. 8A and 8B show movement of the human wrist, in accordance with one or more embodiments.
Figure 8B:
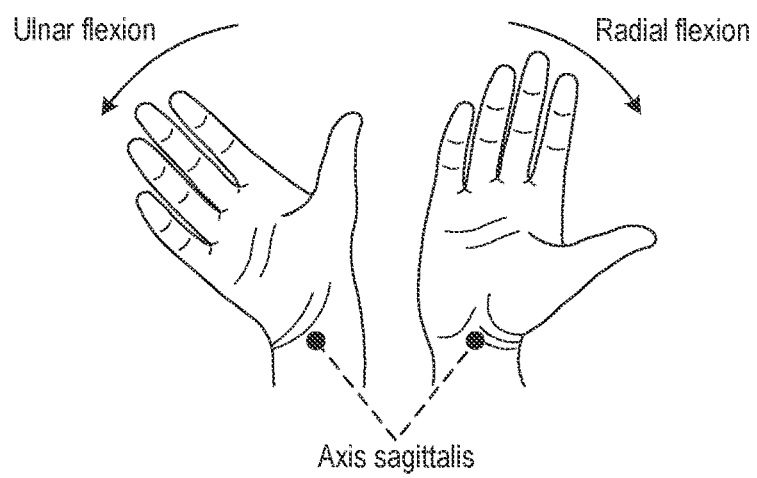

FIG. 7 shows movement of the human ankle, in accordance with one or more embodiments. FIGS. 8A and 8B show movement of the human wrist, in accordance with one or more embodiments. The systems disclosed herein can develop surgical plans to achieve the targeted motion and can simultaneously display pre-operative biomechanics and intraoperative biomechanics, pre-operative renderings of the surgical site and captured images of the surgical site, captured images of the surgical site and metrics, or combinations thereof. This allows a user to evaluate the accuracy of pre-operative predictions, progress of the surgical procedure, and/or real-time monitoring of metrics. For example, a user can input one or more target outcome values, such as the number of degrees of freedom, range of motion, maximum/minimum motion/joint angles, or the like. The system can then perform any number of simulations using one or more virtual models to generate a surgical plan that meets the user inputted target outcome values.

Advantageously, surgical steps can be generated and provided to a surgical system to perform the procedure to meet the predicted outcomes based on soft tissue compliance, joint mechanics, loading, activities performed by patient, etc. The system can then update surgical plans to achieve the target outcome values and/or other user input. The number and position of anchor points, connections, and other features of the tethering can be selected to achieve the outcome criteria. For example, prior to conducting a surgery, the systems disclosed herein can simulate the mobility (e.g., sit, stand, walk, etc.) of the patient after the surgery.

FIG. 7 shows tethering 702, 704 (via anchors and sutures) that can stabilize the joint 710. Virtual connections 702, 704 can be used in simulations to generate values or metrics for the ankle. For example, the values can include, for example, angles of abduction, dorsiflexion, plantarflexion, eversion, inversion, and/or other metrics, which can be displayed for evaluating predicted outcomes. The system can move tethering in a virtual model to perform additional simulations. For example, the tethering 702, 704 can be moved to another location, as illustrated by arrows 712, 714, respectively. The change in biomechanics based on a modification can be illustrated for viewing. For example, the change in the abduction, adduction dorsiflexion, plantarflexion, eversion, and/or inversion can be calculated and displayed.

By way of example, the pre-operative range of motion of the ankle can be, for example, dorsiflexion of 20°-30°, plantarflexion of 40°-50°, inversion/eversion of 30°, supination of 5°, or other ranges of motion. The change in tethering positions can result in an angle change of abduction of about 10° in either direction, angle of dorsiflexion of 10°, plantarflexion angle of 5°, eversion angle of 3°, and/or inversion angle of 5°. Bone-ligament tethering of ankle structures can be selected to achieve one or more of target outcome values. A user can move the location of the tethering to see the effects with joint movement in real-time.

Referring to FIGS. 8A and 8B, bone-ligament tethering, or other surgical steps, can be generated to modify the wrist to achieve one or more of target outcome values. A user can input target outcome values, such as a flexion of 80°–90°, extension of 75°-85°, radial flexion of 20°-22°, ulnar flexion of 35°, or other ranges of motion or values.

Virtual models and simulations disclosed herein can be performed to generate the surgical plans for the Figures herein. 3D images generated can be of the virtual model, simulated virtual steps of the procedure, and other images associated with the model/simulation. In some procedures, a computer-aided design (CAD) graphical user interface (GUI) receives images of the patient's anatomy and generates virtual two-dimensional or three-dimensional models with surface topologies, tissue properties, boundary conditions, etc. The models can represent anatomical features of interest, including skin, bones, soft tissue, fluids, connective tissue, and ligaments using the embodiments, methods, and features disclosed herein. The embodiments, methods, and features disclosed herein can be used to implement the examples discussed below.

In some virtually simulated leg procedures, an incision is made from a tip of the fibula to the extensor retinaculum of the virtual model. Virtual holes can be drilled in structures, such as the fibula, to place virtual drill guides, anchors, and other features along the anatomy. Multiple positions of fibula anchors can be analyzed to select a target fibula anchor position. One or more sutures can pass through the fibula anchor and be connected to another structure, such as ligaments (e.g., extensor retinaculum). The suture can then be routed back and returned to the anchor. In this manner, the fibula anchor can be used to limit motion of another structure. The system can analyze the characteristics and properties of the extensor retinaculum based on, for example, X-ray images, MRIs, and other patient images. Ankle simulations can be performed to, for example, select the number and locations of the anchors and sutures extending through, under, and/or above the extensor retinaculum.

Anchoring of the extensor retinaculum can cause tendons of the extensor muscles to be pulled inwardly toward the fibula. This can cause tensioning of the tendons of the peroneus tertius and the extensor digitorum longus. The alterations to the tendons can be virtually simulated based on the virtual tensioning of the sutures. This allows for virtual simulations of movement of a joint under loading, performing pre-defined determined tasks, etc. The tensioning of the extensor retinaculum can be increased or decreased to increase or decrease, respectively, the tensioning of the underlying tendons. Three-dimensional modeling analyses can be performed to accurately determine procedures to be performed based on the tensioning. In some procedures, additional or ancillary procedures can be performed to further adjust the procedure.

Additional anchors can be positioned along the leg. By way of example, a calcaneus anchor can be attached to the calcaneus bone. One or more sutures can be connected to the calcaneus anchor and connected to the extensor retinaculum (e.g., superior extensor retinaculum, inferior extensor retinaculum, etc.) one or more times in, for example, a weaving fashion, an overlapping fashion, or the like. The suture can then be attached to the fibula anchor, the calcaneus anchor, or another anchor. Tensioning of the extensor retinaculum can alter underlying tissue by, for example, tensioning one or more of the longus tendons. The number of anchors, number of times the suture passes through or is connected to the ligament, and other parameters can be selected based on the targeted outcome. Advantageously, overall motion of the joint can be analyzed based on multiple connections between multiple anatomical structures of the joint or structures surrounding the joint. The output from the simulations can be displayed for movements of the anatomy as illustrated in FIGS. 7-8B. A user can modify, adjust, and/or input values for the patient databases to perform additional simulations to generate predicted outcomes and confidence scores.

Inter-operative data can be compared to the predicted data in the patient databases. If differences between the predicted data and the actual data exceed a threshold, one or more warnings can be sent to the user or the robotic system. The surgical procedure can be adjusted to compensate for the changes. In some embodiments, the user can stop the procedure to perform alternative steps or evaluation based on the alert. The thresholds for alerts can be selected using machine learning models trained based on previous procedures. This allows alerts to be accurately generated.

The virtual robotic surgical procedures disclosed herein can be performed using simulation and computer-aided design. For example, the virtual robotic surgical procedure is performed using the one or more processors to aid in the creation, modification, analysis, or optimization of implants and tools, and to create a database for manufacturing. Further, the virtual robotic surgical procedure can use vector-based graphics to depict the surgical implants, and can also produce raster graphics showing the overall appearance and path of the surgical implant in the virtual robotic surgical procedure. Moreover, the output of the virtual robotic surgical procedure can convey information, such as processes, dimensions, and tolerances, according to application-specific conventions. The virtual robotic surgical procedure can be used to design curves and figures in two-dimensional space or curves, surfaces, and solids in three-dimensional space, and to rotate and move a virtual model of the surgical implant for viewing. For example, virtual joints can be generated for 2D or 3D spaces.

Simulations for the virtual robotic surgical procedure can be performed using virtual models that can include two- or three-dimensional models to evaluate, for example, one or more steps of a surgical procedure (or entire procedure), predicted events, outcomes, etc. The simulations can be used to identify and assess biomechanics, access paths, stresses, strains, deformation characteristics (e.g., load deformation characteristics, load distributions, etc.), fracture characteristics (e.g., fracture toughness), fatigue life, etc. The virtual model can include a model of the patient's anatomy, implant(s), end effectors, instruments, access tools, or the like. The one or more processors can generate a three-dimensional mesh to analyze models. Machine learning techniques can be used to create an optimized mesh based on a dataset of joints, anatomical features, and implants, or other devices. The three-dimensional models, surfaces, and virtual representations can be generated by CAD software, FEA software, and robotic control software/programs based on patient data (e.g., images, scans, etc.), implant design data, or the like. A user can view, manipulate (e.g., rotate, move, etc.), modify, set parameters (e.g., boundary conditions, properties, etc.), and interact with the models. The control parameters, robotic kinematics, and functionality can be used to generate the simulations. In some embodiments, models of end effectors of a robotic system are generated to perform virtual procedures on virtual anatomical models. Virtual simulations of surgical procedures in which a user selected robotic surgical steps and physician steps can be used to generate, modify, and select surgical plans, surgical robot configurations, or the like.

Pre-operative simulations can be performed for different surgical robots using pre-operative patient data (e.g., pre-operative scans, images, etc.). A surgical robot for performing a surgical procedure or portion thereof can be selected based on the simulation(s). This allows a healthcare provider to select a surgical robot suitable for a particular procedure. Additionally, the simulations can be used to generate, modify, and/or verify surgical plans. In some embodiments, a configuration of the surgical robot is selected based on the simulations. For example, multiple simulations can be performed for a surgical robot in different configurations (e.g., the surgical robot having different end effectors) and using different surgical techniques. The healthcare provider can select the surgical robot configuration and surgical plan based, at least in part, on the simulations. End effectors and tools of the surgical robot, imaging equipment, and manual equipment can be selected based on the simulations.

In some embodiments, the surgical system can perform virtual simulations based on one more design parameters, including simulation time, resource usage, accuracy level, and/or data output. The simulation time can be selected so that the virtual simulation is completed within a time period (e.g., percentage of completion time for a surgical step, percentage of surgical procedure duration, user-input time period, etc.). The complexity of the models can be increased or decreased to decrease or increase, respectively, the simulation time period. If the user requests a significant amount of data output (e.g., joint mechanics, loads applied to anatomical structures, multiple implants, fatigue life, etc.), high complexity models (e.g., FEA models with a large number of elements/nodes, optimization models, fluid flow models, etc.) can be generated. Resource usage parameters can be used to select features of three-dimensional models of the anatomy and implants based on available processing resources, including central processing unit (CPU) cycles, memory space, network bandwidth, or a combination thereof. For example, the resource usage parameters can be set to limit usage of such processing resource(s). The surgical system can perform one or more corrective measures to free up the amount of resources required to enable process resources to be available to the robotic apparatus to complete tasks. The corrective measures can include one or more of allocating memory space, prioritizing packets, limiting CPU usage, and/or throttling bandwidth (e.g., throttling network bandwidth). The complexity and features (e.g., surface contours, feature matching, etc.) can be selected based on the available computing resources.

The surgical system can determine the simulation time period based on an action schedule of the surgical plan, a time allocated for the at least one robotic surgical action to be planned and completed, etc. The virtual simulations can be performed while one or more instruments are at least partially positioned within a patient to complete a current surgical action. This allows simulations to be performed concurrently with surgical actions on the patient. Suturing tools, anchoring tools, bronchoscopes, endoscopes, and/or imaging equipment are at least partially positioned within the patient to obtain the intraoperative patient data.

Virtual surgical procedures can include one or more robotic assisted surgical steps, automated surgical steps, and/or physician-controlled surgical steps. Intraoperative virtual simulations can be performed at any time during a surgical procedure to plan future surgical steps or actions. The system can collect real-time surgical data, patient data, or other information continuously or periodically before, after, and/or during surgical steps. Surgical plans can be modified based on intraoperative planning, trained machine learning models, virtual simulations, etc., and obtained data, such as pre-operative data, intraoperative data (e.g., surgical robot data, patient data, etc.), and/or other data. In some embodiments, virtual simulations are performed based on intraoperative patient data. The virtual simulations can be used to generate one or more robotic surgical actions for an intraoperative surgical plan using a trained machine learning model. The surgical system can control a robotic surgical apparatus to perform the robotic surgical action according to the intraoperative surgical plan. Planned robotic surgical actions can be generated any number of times to dynamically modify the intraoperative surgical plan. The real-time planning enables one or more trained machine learning models to determine surgical steps based on the current status of the patient, functionality of the surgical robotic apparatus, etc. If the surgical robotic apparatus is not configured for performing surgical action(s), a user can be notified that the configuration of the surgical robotic apparatus should be modified by, for example, changing end effectors, installing new instruments, etc. Once reconfigured, the surgical robotic apparatus can continue in autonomous mode, semi-autonomous mode, or another mode.

In some embodiments, the processes described herein are performed by the modules described. In other embodiments, the processes are performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

Figure 9:
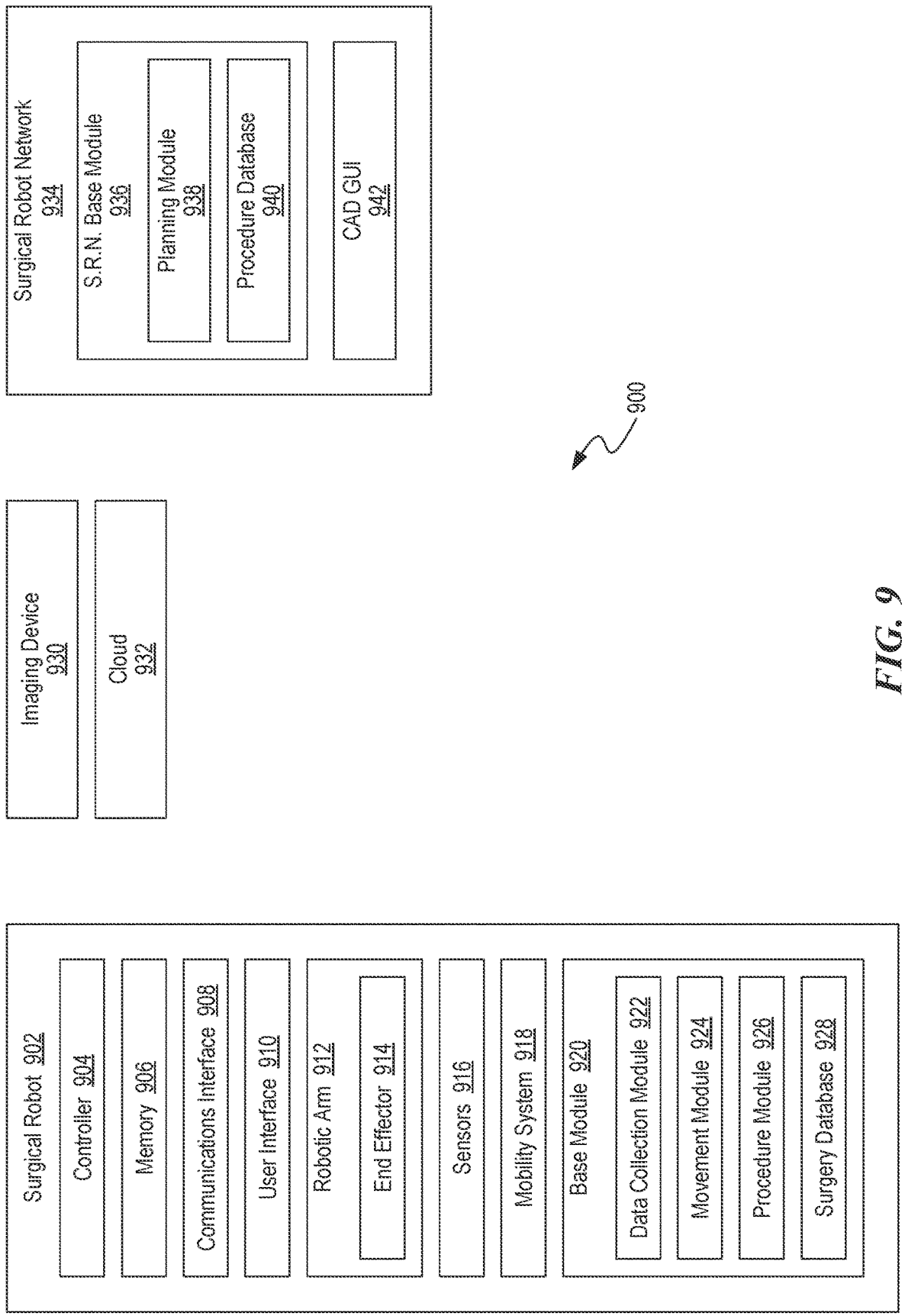
FIG. 9 illustrates a surgical robot with extended operational range, according to an embodiment.

FIG. 9 illustrates a surgical robot 902 with extended operational range according to an embodiment. Surgical robot 902 is a robotic system designed to perform or assist a surgeon in performing a surgical operation on a patient. System 900 is the same as or similar to the robotic surgical system 160 illustrated, and described in more detail with reference to FIG. 1, and robotic surgical system 400 discussed in connection with FIG. 4A. System 900 can include components and features discussed in connection with FIGS. 1-3 and 4B-5. For example, system 900 can include a console with features of the console 108 of FIG. 1.

Surgical robot 902 may include a controller 904, memory 906, and at least one robotic arm 912 with an end effector 914. The surgical robot 902 may further include a user interface 910 for accepting control inputs from a user, such as a surgeon or other medical professional and a communications interface 908 for transmitting and receiving data to and from a cloud 920 for the purpose of training an artificial intelligence operating within the surgical robot or receiving remote commands from a remote user or an artificial intelligence existing external to the surgical robot 902 (see FIG. 2).

Surgical robot 902 can include multiple sensors 916 for providing feedback to the user or an artificial intelligence. A controller 904 is a computing device comprised of a processor for performing computations and communicates with a memory 906 for storing data. The controller 910 is in communication with communications interface 912 and may further be allowed to control at least one robotic arm 912 and end effector 914 of surgical robot 902. The controller may be a commercially available central processing unit (CPU) or graphical processing unit (GPU) or may be a proprietary, purpose-build design. More than one controller 904 may operate in tandem and may be of different types, such as a CPU and a GPU. A GPU is not restricted to only processing graphics or image data and may be used for other computations.

Memory 906 is the electronic circuitry within a computing device that temporarily stores data for usage by the controller 904. The memory 906 may additionally comprise persistent data storage for storing data used by the controller 904. The memory 906 may be integrated into a controller 904 or may be a discrete component. The memory 906 may be integrated into a circuit, such as soldered on component of a single board computer (SBC) or may be a removable component such as a discrete dynamic random-access memory (DRAM) stick, secure digital (SD) card, flash drive, solid state drive (SSD), magnetic hard disk drive (SSD), etc. In some embodiments, memory 906 may be part of a controller 904. Multiple types of memory 906 may be used by surgical robot 902.

Communications interface 908 allows surgical robot 902 to communicate with external devices and may comprise a wireless antenna and transceiver or a port for receiving a cable to facilitate a wired connection. Examples of a wired connection include ethernet, universal serial bus (USB) or a proprietary connection. A wireless communications interface 912 may include any of Wi-Fi, Bluetooth, near field communications (NFC) or a cellular communications interface such as 3G, 4G, LTE, or 5G. The communications interface 912 may connect a user interface 910 to the surgical robot 902 or may facilitate access to a local network or a cloud network to access a remote server and/or database.

User interface 910 is a means of interacting with a surgical robot 902 and may include any of a keyboard, computer mouse, trackball, joystick, wireless or wired gamepad, sliders, scroll wheels, touch screen or microphone for receiving voice commands. The user interface 910 may additionally comprise any method of interaction of a user with a surgical robot 902 not listed. The user interface 910 may accept direct inputs, such as from a joystick controlling the movement of a robotic arm or indirect inputs such as commands entered on a keyboard or touch screen such as adjusting the sensitivity of a joystick control or the speed of a robotic arm's 912 movement in response to a joystick. The user interface 910 may also comprise a screen for presenting information to the user such as patient status, imaging data, and navigational data and speakers for providing auditory feedback. The user interface 910 may also utilize haptics to provide feedback to the user. In additional embodiments, the user interface 910 may comprise an augmented reality (AR) or virtual reality (VR) headset to enable a surgeon to view imagery from at least one imaging device 930 in real-time and may additionally comprise an overlay, such as highlighting the blood vessels comprising a path in which the catheter must be advanced to access the treatment site, such as a blood clot. The user interface 910 may additionally comprise voice or eye tracking controls.

Robotic arm 912 is a mechanically actuated arm or lever with at least two degrees of freedom. A robotic arm 912 will typically include at least one end effector 914 or an imaging device 926 and may include both an end effector 914 and an imaging device 930. The robotic arm 912 may additionally be capable of changing the end effector 914 to facilitate multiple functions and operation of a variety of tools. The robotic arm 914 may be manually controlled or operated in an autonomous or semi-autonomous mode. A surgical robot 902 may have one robotic arm 912 or multiple robotic arms 912, each of which may be operated independently by one or more users or autonomous systems or a combination of users and autonomous systems. In some embodiments, robotic arm 912 communicates with mobility system 918 to indicate that robotic arm 912 is performing a function of the medical procedure.

Mobility system 918 is sometimes referred to as a "mobile unit." An example of mobile unit 446 is illustrated with reference to FIG. 4A. The mobile unit 446 can include actuators, wheels 444, and a motor 442. Example wheels 444 and an example motor 442 are illustrated with reference to FIG. 4A. Robotic arm 912 can communicate with mobility system 918 using a digital bitstream or a digitized analog signal over a point-to-point or point-to-multipoint communication channel. Examples of such channels are copper wires, optical fibers, wireless communication using radio spectrum, storage media and computer buses. The data are represented as an electromagnetic signal, such as an electrical voltage, radio wave, microwave, or infrared signal.

In embodiments, analog transmission (a method of conveying voice, data, image, signal or video information using a continuous signal which varies in amplitude, phase, or some other property in proportion to that of a variable) is used. The messages are either represented by a sequence of pulses by means of a line code (baseband transmission), or by a limited set of continuously varying waveforms (passband transmission), using a digital modulation method. Data transmitted may be digital messages originating from robotic arm 912, or an analog signal such as a video signal, digitized into a bit-stream, for example, using pulse-code modulation or more advanced source coding schemes. The communication prevents mobility system 918 from activating. In some embodiments, navigating mobility system 918 includes causing robotic arm 912 and end effector 914 to remain stationary while surgical robot 902 moves from a first location to a second location. For example, robotic arm 912 remains in a stationary position while mobility system 918 moves the base of surgical robot 902. In some embodiments, the navigating mobility system 918 can move a portion of the patient and the surgical robot 902 can be stationary. For example, a portion of the patient can be moved from a first location to a second location using a movable table (e.g., a surgical table supporting the patient).

In some embodiments, the first and/or the second location is based on a surgical plan. Surgical plans are described in more detail with reference to FIGS. 4A, 4B, and 5. The surgical plan can indicate an optimal location for planned surgical steps, functionality of surgical robot 902 (e.g., a range of motion or degrees of freedom), and/or surgical steps to be performed. A pre-operative surgical plan can indicate positions and orientations for surgical robot 902, a surgical room layout, and changes to positions of a patient surgical bed or equipment. An example operating room 102 including a surgical bed and example medical equipment are illustrated and described in more detail with reference to FIG. 1. The machine learning module 200 (illustrated and described in more detail with reference to FIG. 2) can be used to generate repositioning instructions for surgical robot 902 to optimize outcomes (determined based on simulations) for surgical steps.

End effector 914 is the end of a robotic arm 912 which is conducting work. The end effector 914 is typically a tool or device for interacting with a physical object and may be a surgical tool intended for acting upon or within a patient or may be a gripping device for securing a separate surgical tool to a robotic arm 912. The end effector 914 may be permanently affixed to the end of a robotic arm 912 or may be detachable allowing for a system of interchangeable end effectors 914 which may alternatively be selected and swapped by a single robotic arm 912 or multiple robotic arms 912. The end effector 914 may comprise a catheter or other tool for accessing a treatment site within a patient. Similarly, the end effector 914 may relate to a deployable device, such as a stent, prior to deployment in a patient.

End effector 914 may be constructed of materials which intentionally absorb, reflect, or are transparent to X-Rays to facilitate the end effector's 914 visibility when viewed using angiography, fluoroscopy, or other imaging modalities, or alternatively, allow the X-Rays to pass through to prevent their interference in images. In some embodiments, the end effector 914 may be made to be selectively transparent to X-Rays such as by changing the profile of the end effector 914 or X-Ray absorbing or reflective components to increase or reduce their visibility to an imaging device 930.

Sensor 916 is a measurement tool for monitoring a characteristic or metric associated with a surgical robot 902, end effector 914 or patient. A sensor 914 may be discrete or part of an array or assembly, such as integrated into a catheter. One or more of the sensors 914 may include an electrophysiologic sensor, a temperature sensor, a thermal gradient sensor, a barometer, an altimeter, an accelerometer, a gyroscope, a humidity sensor, a magnetometer, an inclinometer, an oximeter, a calorimetric monitor, a sweat analyte sensor, a galvanic skin response sensor, an interfacial pressure sensor, a flow sensor, a stretch sensor, a microphone or any combination thereof, etc. The sensors 916 may be integrated into the operation of the surgical robot 902 or may monitor the status of a patient. The data acquired by the sensors 916 may be used to train a machine learning algorithm used by the surgical robot 902 or artificial intelligence to control the surgical robot 902.

Sensors 916 may additionally comprise an X-Ray dosimeter to monitor the intensity of X-Rays being emitted toward the patient to prevent excessive doses of radiation. The sensors 916 may be utilized to reduce the intensity of the X-Rays or reduce the duration or increase the interval in which the X-Rays are emitted toward the patient to control the dose throughout a procedure.

The computer-implemented methods disclosed herein implement control and navigation of a robotic surgical apparatus (e.g., surgical robot 902). A computer system (e.g., S.R.N. 934) positions the robotic surgical apparatus at a first location in an operating room. The robotic surgical apparatus comprises a mobile unit (e.g., mobility system 918) configured to move the robotic surgical apparatus, robotic arm 912, and end effector 914 attached to the robotic arm 912. At least one of a portion of an anatomy of a patient or an instrument for a surgical step to be performed on the portion of the anatomy, by the robotic surgical apparatus, is unreachable by end effector 914 when the robotic surgical apparatus is positioned at the first location.

Mobility system 918 includes elements enabling movement of surgical robot 902, for example, actuators, wheels 444, and at least one motor 442. Example wheels 444 and an example motor 442 are illustrated with reference to FIG. 4A. For example, an actuator moves and controls a mechanism of surgical robot 902. An actuator is enabled by a control device (controlled by control signal), which can be an electric voltage or current, pneumatic, or hydraulic fluid pressure. The wheels 444 can be omnidirectional using tracks. In embodiments, Mobility system 918 includes dedicated sensors or processing abilities, and communicates with surgical robot 902 to enable coordination at least one robotic arm. Mobility system 918 can receive user input data from CAD GUI 942 to determine movements required by surgical robot 902.

In embodiments, surgical robot 902 receives instructions to move from a first location to a second location in an operating room. Navigation of surgical robot 902 can be based on camera images, LIDAR, or sensors using one or more cameras, image recognition devices, ultrasonic sensors, infrared sensors, or positioning devices incorporated into surgical robot 902 and/or surgical room layouts or navigation techniques (e.g., visual simultaneous location and mapping techniques) to avoid hitting objects or personnel. In some embodiments, the computer system synchronizes steps of the surgical plan with the surgical environment. The computer system can also notify the surgical team to move the patient, surgical bed, and/or other items in the surgical room. The surgical robot 902 can reposition itself based on real-time input (e.g., captured images, LIDAR signals, etc.) to navigate through the surgical environment and position its robotic arms and end effectors at optimal positions. For example, the computer system can for example, detect, an obstruction a robotic arm before or while the robotic surgical apparatus performs a surgical step, compensate for the obstruction (e.g., modify the surgical step or plan and cause the robotic surgical apparatus to continue performing the surgical step or plan), indicate the presence of the obstruction, and/or determine absence of the obstruction. Example cameras, sensors, and an operating room 102 are illustrated and described in more detail with reference to FIG. 1.

For example, movements for surgical robot 902 are received from a data file containing movement instructions, e.g., 3 feet straight ahead, rotate 90 degrees, 2 feet straight ahead. In embodiments, a portion of the instructions are indicated by a user using a computer-aided design (CAD) graphical user interface. Surgical robot 902 can use markers on a floor of the operation room 102, e.g., quick response (QR) codes, labels, or arrows to identify a path to a particular anatomical region of a patient. The QR code can be a matrix barcode (or two-dimensional barcode) that is a machine-readable optical label. The QR code stores information about a locator, identifier, or tracker that points to the particular anatomical region of a patient. For example, the particular anatomical region of a patient can be a left-side head-level, a left-side torso-level, a left-side leg-level, a left-side foot-level, etc. In embodiments, mobility system 918 is equipped with multiple sensors, e.g., image recognition devices, ultrasonic sensors, or infrared sensors to detect objects obstructing a path of surgical robot 902. Mobility system 918 can communicate with surgical robot 902 or medical staff to indicate that surgical robot 902 or the medical staff is an obstruction.

For example, Mobility system 918 generates a path from an initial location to a goal location to avoid obstacles. The environment can be modeled in either 2-dimensional or 3-dimensional space. Mobility system 918 determines a set of all configurations of surgical robot 902 as well as the different transformations that can be applied to the robot. Mobility system 918 determines an obstacle space (a set of configurations within the configuration space where the Mobility system 918 is unable to move to). Different path planning methods can be used including Rapidly Exploring Random Tree (RRT), Local path planning, Probabilistic Roadmap (PRM), Evolutionary Artificial Potential Field (EAPF), Indicative Route Method (IRM), Modified Indicative Routes and Navigation (MIRAN).

Base module 920 begins operation by initiating data collection module 122, e.g., using a message, a software or hardware trigger, an interrupt, or another signal. Then the base module 920 extracts the first data entry in the surgery database 928. The base module 920 sends the extracted data entry to the movement module 924. Base module 920 initiates movement module 924, e.g., using a message, a software or hardware trigger, an interrupt, or another signal. Base module 920 sends the extracted data entry to the procedure module 926. Base module 920 initiates the procedure module 926, e.g., using a message, a software or hardware trigger, an interrupt, or another signal. The base module 920 determines if there are any data entries remaining in the surgery database 928. If it is determined that there are data entries remaining in the surgery database 928 the base module 920 extracts the next data entry. If it is determined that there are no data entries remaining, the base module 920 ends. Data collection module 122 is initiated by base module 920, e.g., using a message, a software or hardware trigger, an interrupt, or another signal. The data collection module 122 connects to the S.R.N. base module 936. The data collection module 122 sends a request for the data stored in the procedure database 940.

Data collection module 122 is continuously polling to receive the data stored in the procedure database 940. The data collection module 122 receives the data stored in the procedure database 940. The data collection module 122 stores the received data in the surgery database 928. The data collection module 122 returns to the base module 920. Movement module 924 begins by being initiated by the base module 920, e.g., using a message, a software or hardware trigger, an interrupt, or another signal. The movement module 924 receives the extracted data entry from the base module 920. The movement module 924 determines the current location of the surgical robot 902. The movement module 924 executes the movement action. Then the movement module 924 is continuously polling for obstructions. The movement module 924 determines if an obstruction was detected. If it is determined that an obstruction was detected, then the movement module 924 alerts the user.

If it is determined that an obstruction was not detected or after the user has been alerted and removed the obstruction, the movement module 924 continues executing the movement action. The movement module 924 determines if the movement action is complete. If it is determined that the movement action is not complete, then the movement module 924 continues to poll for obstructions. If it is determined that the movement action is complete the movement module 924 sends the completion status to the procedure module 926. The movement module 924 returns to the base module 920. Procedure module 926 begins by being initiated by base module 920, e.g., using a message, a software or hardware trigger, an interrupt, or another signal. Procedure module 926 receives the extracted data entry from the base module 920. The procedure module 926 determines if the completion status was received from the movement module 924. If the procedure module 926 determines that the completion status was not received from the movement module 924 then the procedure module 926 is continuously polling to receive the completion status from the movement module 924 and returns to receiving the data entry from the base module 920.

If the completion status was received, then the procedure module 926 receives the completion status from the movement module 924. The procedure module 926 extracts the procedure data file from the data entry. The procedure module 926 sends the procedure data file to the end effector 914. The procedure module 926 executes the procedure data file. The procedure module 926 returns to the base module 920. Surgery database 928 can store data describing a patient ID, a type of surgery, or a 3D rendering of a patient's medical images. Surgery database 928 can store data describing a starting position of the surgical robot 902, the ending location of the surgical robot 902, or a movement data file, which contains the movements required by the surgical robot 902 to move from the starting position to the ending position. Surgery database 928 can store data describing a process required for the surgery, techniques required for the surgery, or tools 154 required for the surgery.

Surgery database 928 can store data describing data files for replays of a step as input into CAD GUI 942, (x, y, z) coordinates of a patient's body, or techniques used (e.g., a threading technique used in the surgery). Surgery database 928 can store data describing data files for the robotic movements of the process or techniques, calculations (e.g., forces required in certain steps or techniques), or materials required for certain steps or techniques. Surgery database 928 can store data describing specialists required for the specific steps or techniques.

In some embodiments, the database may contain staging areas for surgical robots 902, active working areas, and their corresponding range of motion. For example, a staging area is a location at which surgical robots 902, medical personnel, equipment, or material are assembled before use. In embodiments, the base and robotic arm 912 are capable of moving independently, such that when the base moves, the robotic arm maintains its position and orientation. By maintaining the position and orientation, surgical robot 902 is enabled to make room for additional equipment or personnel or to increase the reach of the robot while not disrupting the procedure. In embodiments, multiple surgical robots coordinate with multiple routines, which enable the surgical robots to stage out of the way and approach the operating table only when required. Routines can be preprogramed or triggered by a surgeon. The surgical robots can navigate around surgical staff and other equipment, and can request other movable surgical robots or surgical staff to move. In embodiments, if a user, such as the surgeon or physician, adjusts or updates a process or technique, the updated process or technique is stored in the surgery database 928.

Data describing a surgical procedure to stabilize an ankle can be stored in surgery database 928. In a surgical procedure, a patient is prepped and draped. Arthroscopic debridement takes place of the ankle joint. An incision is made from a tip of a fibula to an extensor retinaculum. A drill hole is made into a calcaneus and an anchor is placed. A suture is then sewn into the extensor retinaculum. A drill hole is made into the fibula and an anchor is placed. The suture limbs from the anchors are tied to bring the ankle mortise into a neutral position to stabilize the ankle joint.

Imaging device 930 refers to any device capable of collecting data which can be used to create an image, or a representation of a physical structure or phenomena. An imaging device 930 may include any device capable of detecting sound or electromagnetic waves and assembling a visual representation of the detected waves. Imaging device 930 may collect waves from any part of the electromagnetic spectrum or sounds at any range of frequencies, often as a matrix of independently acquired measurements which each representing a pixel of a two or three-dimensional image. These measurements may be taken simultaneously or in series via a scanning process or a combination of methods. Some pixels of an image produced by an imaging device 930 may be interpolated from direct measurements representing adjacent pixels in order to increase the resolution of a generated image. Imaging device 930 may receive or generate imaging data from a plurality of imaging devices 930.

Imaging devices 930 can include cameras attached to the robotic arm 912, cameras mounted to the ceiling or other structure above the surgical theater, cameras that may be mounted on a tripod or other independent mounting device, body cameras that may be worn by the surgeon or other surgical staff, cameras that may be incorporated into a wearable device, such as an augmented reality device like Google Glass, Microsoft HoloLens, etc., cameras that may be integrated into an endoscopic, microscopic, laparoscopic, or any camera or other imaging device 930 (e.g. ultrasound) that may be present in the surgical theater. Imaging device 930 can include an algorithm or software module capable of determining qualitative or quantitative data from medical images, which may be, for example, a deep learning algorithm that has been trained on a data set of medical images. An imaging device 930 may further refer to a device used to acquire medical imagery by any means including magnetic resonance imaging (MRI), computed tomography (CT), X-Ray, positron emission tomography (PET), ultrasound, arthrography, angiography, fluoroscopy, myelography, etc. An imaging device 930 may acquire images in real-time or be used to create composite images or models in real-time.

Cloud 932 is a distributed network of computers comprising servers and databases. Cloud 932 can be a private cloud, where access is restricted by isolating the network such as preventing external access, or by using encryption to limit access to only authorized users. Alternatively, cloud 932 may be a public cloud where access is widely available via the internet. A public cloud may not be secured or may include limited security features. Surgical robot network (SRN) 934 is a network connected to surgical robot 902 in which the surgical robot may receive and send data, provide controls to a user for the surgical robot 902 through a user interface 910, and allow a user to utilize a CAD GUI 946 to design, test, and create a surgical process for a patient.

S.R.N. base module 936 begins by initiating the planning module 938, e.g., using a message, a software or hardware trigger, an interrupt, or another signal. The S.R.N. base module 936 connects to the data collection module 122. The S.R.N. base module 936 is continuously polling for a request for the data stored in the procedure database 940. The S.R.N. base module 936 receives a request for the data stored in the procedure database 940 from the data collection module 920. S.R.N. base module 936 sends the data stored in the procedure database 940 to the data collection module 122, and initiates the planning module 938, e.g., using a message, a software or hardware trigger, an interrupt, or another signal.

Planning module 938 begins by being initiated by the S.R.N. base module 936, e.g., using a message, a software or hardware trigger, an interrupt, or another signal. The planning module 938 queries the procedure database 940 for the first entry. The planning module 938 extracts the data entry from the procedure database 940. The planning module 938 displays the data entry on the CAD GUI 942. The user inputs the robotic movements and locations needed for the surgical robot 902 for the data entry. The planning module 938 stores the movements and locations in the procedure database 940. The planning module 938 determines if there are data entries remaining in the procedure database 940. If it is determined that there are data entries remaining in the procedure database 940 the planning module 938 queries the procedure database 940 for the next entry and continues to extract the data entry. If it is determined that there are no data entries remaining in the procedure database 940 the planning module 938 returns to the S.R.N. base module 936.

Procedure database 940 can store data describing a patient ID, a type of surgery, or a 3D rendering of a patient's medical images. Procedure database 940 can store data describing a starting position of surgical robot 902, an ending location of surgical robot 902, or a movement data file that stores movements required by the surgical robot 902 to move from the starting position to the ending position. Procedure database 940 can store data describing a process required for a surgery, techniques required for the surgery, or tools 154 required for a surgery. Procedure database 940 can store data describing a data file for a procedure or technique, data files for replays of a step as input into CAD GUI 942, or (x, y, z) coordinates of a patient's body. Procedure database 940 can store data describing techniques used (e.g., a threading technique used in surgery), data files for robotic movements of the process or technique, or calculations (e.g., forces required in certain steps or techniques).

Procedure database 940 can store data describing materials required for certain steps or techniques or specialists required for the specific steps or techniques. Procedure database 940 can store data describing staging areas for surgical robots 902, active working areas, or corresponding range of motion. In some embodiments, the base and robotic arm 912 may be capable of moving independently such that when the base moves, the robotic arm can maintain its position and orientation, allowing the surgical robot 902 to make room for additional equipment or personnel or to increase the reach of the robot while not disrupting the procedure. In some embodiments, the surgical robots 902 may coordinate with multiple routines which allow the surgical robots 902 to stage out of the way and approach the operating table only when required.

Routines may be preprogramed and triggered by a surgeon and the surgical robots 902 may navigate around the surgical staff and other equipment and may request other movable surgical robots 902 and surgical staff to move if necessary. In some embodiments, if the user, such as the surgeon or physician, adjusts or updates the process or technique then the updated process or technique will be stored in the procedure database 940.

CAD GUI 942 is a user interface for a computer software system to design surgical processes for patients. Computer-aided design (CAD) is the use of computers to aid in the creation, modification, analysis, or optimization of a design, such as a surgical procedure. This software is used to increase the productivity of the designer or user, such as a doctor or medical professional, improve the quality of design, improve communications through documentation, and to create a database for the procedure. CAD output is often in the form of electronic files for print, machining, or other manufacturing operations. A GUI or graphical user interface may be an interface(s) may either accept inputs from users or provide outputs to the users or may perform both actions. In one case, a user can interact with the interface(s) using one or more user-interactive objects and devices.

The user-interactive objects and devices may comprise user input buttons, switches, knobs, levers, keys, trackballs, touchpads, cameras, microphones, motion sensors, heat sensors, inertial sensors, touch sensors, or a combination of the above. Further, the interface(s) may either be implemented as a Command Line Interface (CLI), a Graphical User Interface (GUI), a voice interface, or a web-based user interface. The CAD GUI 942 allows a user, such as a surgeon, doctor, medical professional, etc., to view an area of a patient's body that requires surgery in a 3D space. The CAD GUI 942 allows the user to view a 3D model of the operating room in order to input the movements necessary for the surgical robot 902.

For example, the user may determine and input the path the robot needs to perform prior to the step in the procedure in which the surgical robot 902 is required to perform a function. The user may input when and how the surgical robot 902 should move and where it should be positioned to perform a function of the surgery or assist the surgeon. The movements of the surgical robot 902 are stored in the procedure database 940 as a data file containing the movements necessary to move from the starting position to the ending position.

CAD GUI 942 also allows the user to select various tools, materials, and techniques required for the surgery and allows the user to manipulate the tools, materials, and techniques, rendered over the patient's 3D image to perform the processes and steps needed for the surgery in a virtual space. The user's movements and actions are saved and stored in the procedure database 940 through the process described in the planning module 940 to assist the surgeon in performing the surgery or to provide the surgical robot 902 with approximate (x, y, z) coordinates to perform the surgery. The CAD GUI 942 allows other users to view or replay the surgery in the 3D space to alter or adjust movements or actions to perform the surgery. In some embodiments, the CAD GUI 942 may provide the user or surgical robot 902 with a list of materials needed, a list of tools required, a workflow process of the surgical procedure, or a 3D visual replay of the surgical procedure, etc.

Figure 10:
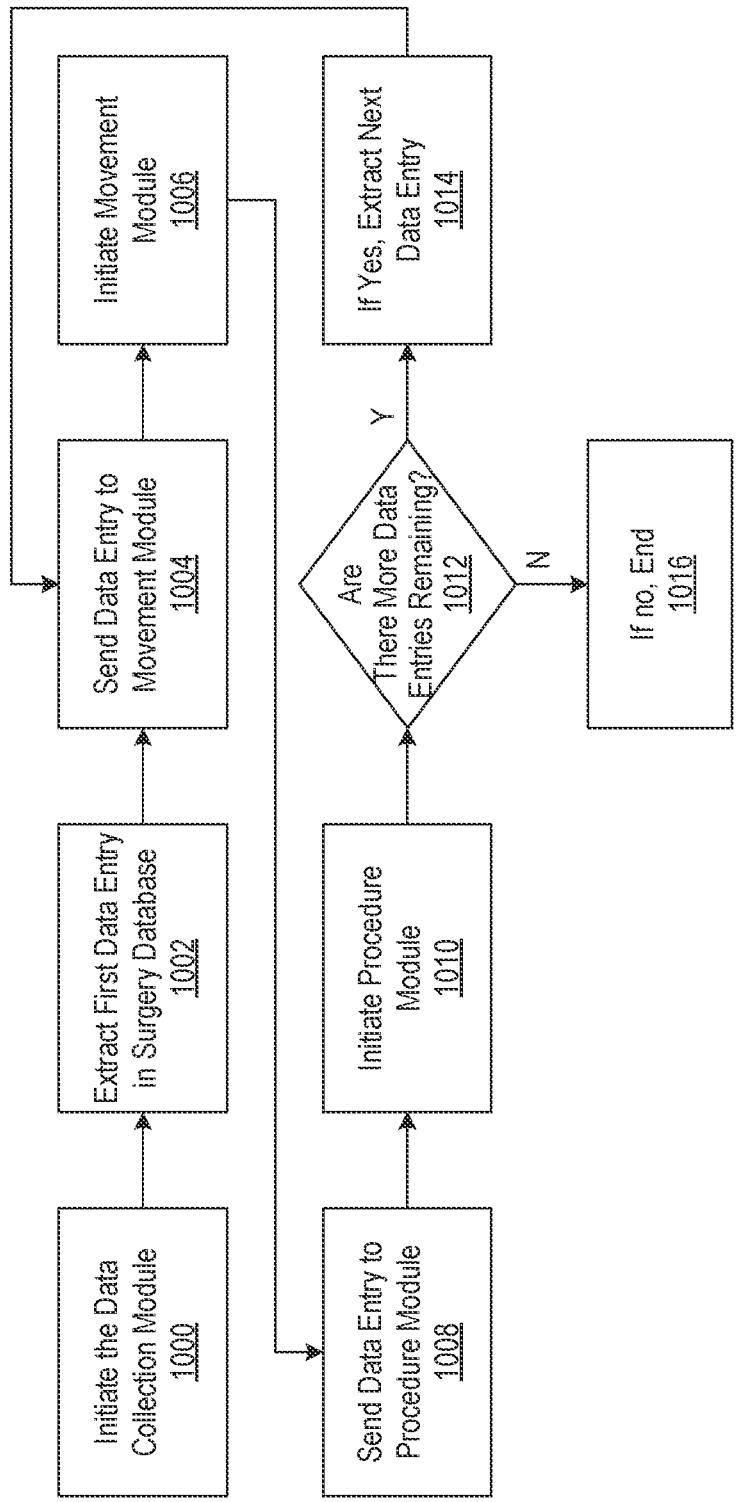
FIG. 10 illustrates a process for a base module, according to an embodiment.

FIG. 10 illustrates a process for base module 920, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The process begins with the base module 920 initiating, at step 1000, the data collection module 122. For example, the data collection module 122 is initiated by the base module 920. The data collection module 122 connects to the S.R.N. base module 936. The data collection module 122 sends a request for the data stored in the procedure database 940.

The data collection module 122 is continuously polling to receive the data stored in the procedure database 940. The data collection module 122 receives the data stored in the procedure database 940. The data collection module 122 stores the received data in the surgery database 928. The data collection module 122 returns to the base module 920.

Then the base module 920 extracts, at step 1002, the first data entry in the surgery database 928. For example, the base module extracts the data entry from the surgery database 928, such as the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

The base module 920 sends, at step 1004, the extracted data entry to the movement module 924. For example, the base module sends the extracted data entry to the movement module 924, such as the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

The base module 920 initiates, at step 1006, the movement module 924. For example, the movement module 924 begins by being initiated by the base module 920. The movement module 924 receives the extracted data entry from the base module 920. The movement module 924 determines the current location of the surgical robot 902. The movement module 924 executes the movement action. Then the movement module 924 is continuously polling for obstructions. The movement module 924 determines if an obstruction was detected. If it is determined that an obstruction was detected, then the movement module 924 alerts the user. If it is determined that an obstruction was not detected or after the user has been alerted and removed the obstruction the movement module 924 continues executing the movement action. The movement module 924 determines if the movement action is complete. If it is determined that the movement action is not complete, then the movement module 924 continues to poll obstructions. If it is determined that the movement action is complete the movement module 924 sends the completion status to the procedure module 926. The movement module 924 returns to the base module 920.

The base module 920 sends, at step 1008, the extracted data entry to the procedure module 926. For example, the base module 920 sends the extracted data entry to the procedure module 926, such as the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

The base module 920 initiates, at step 1010, the procedure module 926. For example, the procedure module 926 begins by being initiated by the base module 920. The procedure module 926 receives the extracted data entry from the base module 920. The procedure module 926 determines if the completion status was received from the movement module 924. If the procedure module 926 determines that the completion status was not received from the movement module 924 then the procedure module 926 is continuously polling to receive the completion status from the movement module 924 and returns to receiving the data entry from the base module 920. If the completion status was received, then the procedure module 926 receives the completion status from the movement module 924. The procedure module 926 extracts the procedure data file from the data entry. The procedure module 926 sends the procedure data file to the end effector 914. The procedure module 926 executes the procedure data file. The procedure module 926 returns to the base module 920.

The base module 920 determines, at step 1012, if there are any data entries remaining in the surgery database 928. If it is determined that data entries remain in the surgery database 928 the base module 920 extracts, at step 1014, the next data entry. For example, for any remaining data entries the base module 920 extracts the next data entry, such as the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques. If it is determined that there are no remaining data entries then the base module 920 ends, at step 1016.

Figure 11:
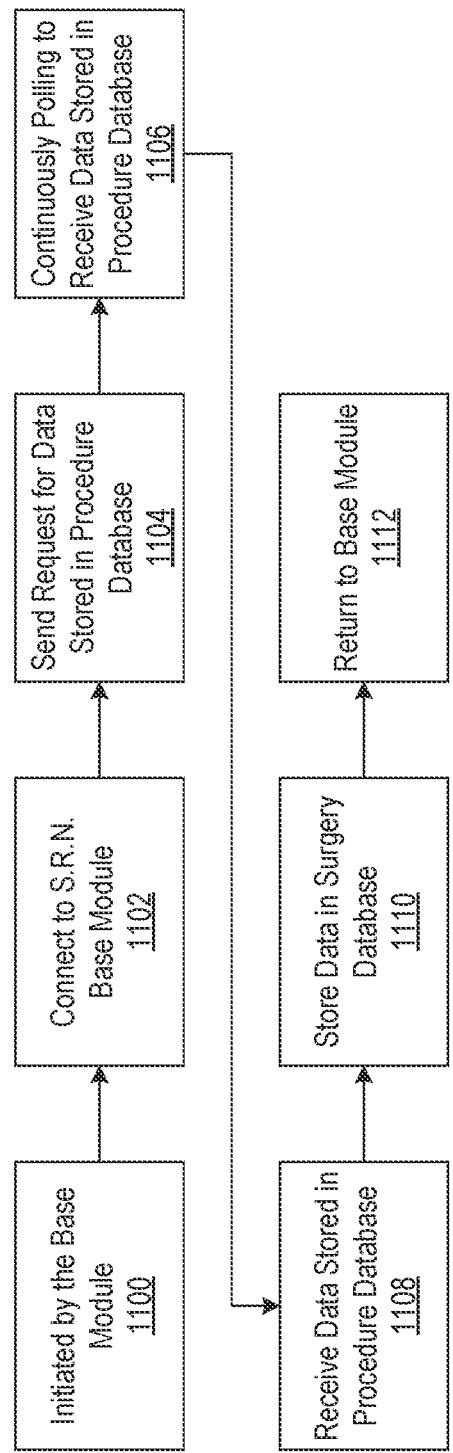
FIG. 11 illustrates a process for a data collection module, according to an embodiment.

FIG. 11 illustrates a process for data collection module 922, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The process begins with the data collection module 922 being initiated, at step 1100, by the base module 920. The data collection module 922 connects, at step 1102, to the S.R.N. base module 936. The data collection module 922 sends, at step 1104, a request for the data stored in the procedure database 940. For example, the data collection module 922 is sending a request to receive the data stored in the procedure database 940 such as, the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

In some embodiments, the database may contain staging areas for surgical robots 902 and active working areas and their corresponding range of motion. In some embodiments, the base and robotic arm 912 may be capable of moving independently such that when the base moves, the robotic arm can maintain its position and orientation, allowing the surgical robot 902 to make room for additional equipment or personnel or to increase the reach of the robot while not disrupting the procedure. In some embodiments, the surgical robots 902 may coordinate with multiple routines which allow the surgical robots 902 to stage out of the way and approach the operating table only when required. Routines may be preprogramed and triggered by a surgeon and the surgical robots 902 may navigate around the surgical staff and other equipment and may request other movable surgical robots 902 and surgical staff to move if necessary.

In some embodiments, if the user, such as the surgeon or physician, adjusts or updates the process or technique then the updated process or technique will be stored in the procedure database 940. For example, for a procedure to stabilize an ankle the process stored in the procedure database 940 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint.

The data collection module 922 is continuously polling, at step 1106, to receive the data stored in the procedure database 940. For example, the data collection module 922 is continuously polling to receive the data, such as the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

The database can contain staging areas for surgical robot 902 and active working areas and their corresponding range of motion. In embodiments, S.R.N 934 causes mobility system 918 to make room for additional equipment or personnel while surgical robot 902 is performing a surgical step. Mobility system 918 is sometimes referred to as a "mobile unit." An example mobile unit 446 is illustrated with reference to FIG. 4A. The mobile unit 446 can include actuators, steering mechanism, navigation system, wheels 444, and a motor 442. Example wheels 444 and an example motor 442 are illustrated with reference to FIG. 4A. The base and robotic arm 912 may be capable of moving independently such that when the base moves, the robotic arm can maintain its position and orientation, allowing the surgical robot 902 to make room for additional equipment or personnel or to increase the reach of the robot while not disrupting the procedure. In some embodiments, the surgical robots 902 may coordinate with multiple routines which allow the surgical robots 902 to stage out of the way and approach the operating table only when required. Routines may be preprogramed and triggered by a surgeon and the surgical robots 902 may navigate around the surgical staff and other equipment and may request other movable surgical robots 902 and surgical staff to move if necessary.

In some embodiments, if the user, such as the surgeon or physician, adjusts or updates the process or technique then the updated process or technique will be stored in the procedure database 940. For example, for a procedure to stabilize an ankle the process stored in the procedure database 940 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint.

The data collection module 922 receives, at step 1108, the data stored in the procedure database 940. For example, the data collection module 922 receives the data, such as the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

In some embodiments, the database may contain staging areas for surgical robots 902 and active working areas and their corresponding range of motion. In some embodiments, the base and robotic arm 912 may be capable of moving independently such that when the base moves, the robotic arm can maintain its position and orientation, allowing the surgical robot 902 to make room for additional equipment or personnel or to increase the reach of the robot while not disrupting the procedure. In some embodiments, the surgical robots 902 may coordinate with multiple routines which allow the surgical robots 902 to stage out of the way and approach the operating table only when required. Routines may be preprogramed and triggered by a surgeon and the surgical robots 902 may navigate around the surgical staff and other equipment and may request other movable surgical robots 902 and surgical staff to move if necessary.

In some embodiments, if the user, such as the surgeon or physician, adjusts or updates the process or technique then the updated process or technique will be stored in the procedure database 940. For example, for a procedure to stabilize an ankle the process stored in the procedure database 940 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint.

The data collection module 922 stores, at step 1110, the received data in the surgery database 928. For example, the data collection module 922 stores the received data in the surgery database 928, such as the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

In some embodiments, the database may contain staging areas for surgical robots 902 and active working areas and their corresponding range of motion. In some embodiments, the base and robotic arm 912 may be capable of moving independently such that when the base moves, the robotic arm can maintain its position and orientation, allowing the surgical robot 902 to make room for additional equipment or personnel or to increase the reach of the robot while not disrupting the procedure. In some embodiments, the surgical robots 902 may coordinate with multiple routines which allow the surgical robots 902 to stage out of the way and approach the operating table only when required. Routines may be preprogramed and triggered by a surgeon and the surgical robots 902 may navigate around the surgical staff and other equipment and may request other movable surgical robots 902 and surgical staff to move if necessary.

In some embodiments, if the user, such as the surgeon or physician, adjusts or updates the process or technique then the updated process or technique will be stored in the surgery database 928. For example, for a procedure to stabilize an ankle the process stored in the surgery database 928 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint. The data collection module 922 returns, at step 1112, to the base module 920.

Figure 12:
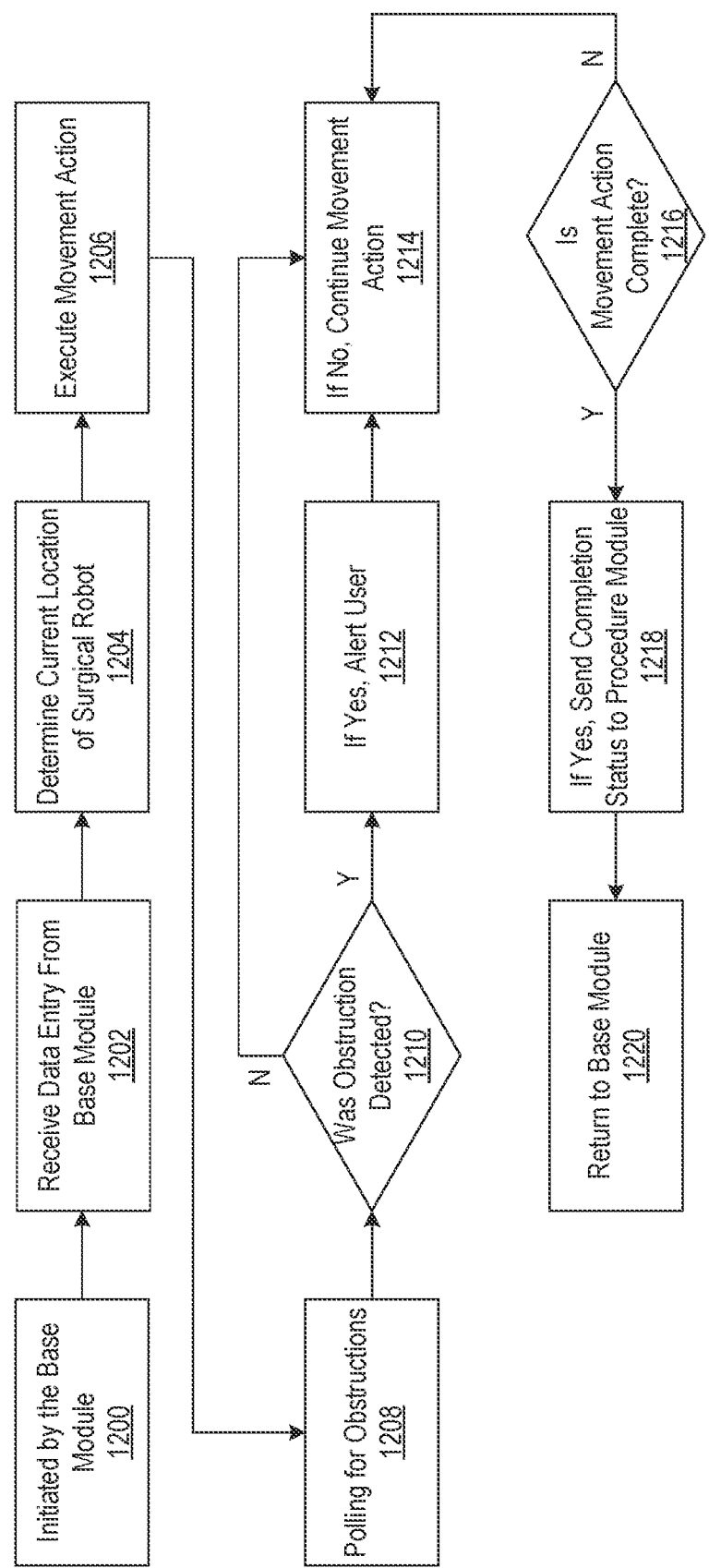
FIG. 12 illustrates a process for a movement module, according to an embodiment.

FIG. 12 illustrates a process for a movement module 924, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the movement module 924. The process begins with the movement module 924 being initiated, at step 1200, by the base module 920. The movement module 924 receives, at step 1202, the extracted data entry from the base module 920. For example, the movement module 924 receives the data entry from the base module 920, which contains the data for the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

The movement module 924 determines, at step 1204, the current location of the surgical robot 902. For example, the movement module 924 may determine the current location of the surgical robot 902 by using sensors of mobility system 918, such as image recognition devices, ultrasonic sensors, infrared sensors, etc. Mobility system 918 is sometimes referred to as a "mobile unit." An example mobile unit 446 is illustrated with reference to FIG. 4A. The mobile unit 446 can include actuators, wheels 444, and a motor 442. Example wheels 444 and an example motor 442 are illustrated with reference to FIG. 4A. Movement module 924 may utilize markers on the operating room floor to determine the current location of the surgical robot 902, such as at docking station, approaching top of the operating table, approaching the bottom of the operating table, approaching left side of the operating table, approaching right side of the operating table, etc. while continuously scanning using the sensors of the mobility system 918 to ensure that the surgical robot 902 will not bump or run into anything in the operating room.

For example, the surgical robot may receive user inputs for the position required for the surgical tool or end effectors and not receive user inputs to position itself throughout the operating room by using the sensors 916 and the mobility system 918. In embodiments, navigating mobility system 918 includes causing mobility system 918 to determine a path to at least one of a portion of an anatomy of a patient or an instrument using at least one of quick response (QR) codes, labels, or arrows posted on a surface of an operating room. For example, there may be markers on the ground, such as QR codes, labels, arrows, etc. to identify a path to certain areas of the patient in which the surgical robot 902 reads the markers and can navigate the operating room to a final position either near or away from the patient depending on the need of the surgical robot 902. For example, if the surgical robot is needed to be on the left side of the patient near the patient's leg there may be markers leading to the left side of the patient and once on the left side the markers may signal to the surgical robot the position relative to the patient, such as head level, upper chest level, lower chest level, upper abdomen level, lower abdomen level, hip level, femur level, knee level, chin or calf level, ankle level, foot level, etc.

In some embodiments, surgical robot 902 does not need user inputted navigation to locate and relocate around the patient during a surgical procedure in which the surgical robot 902 is needed. For example, a pre-operative surgical plan can indicate positions and orientations for surgical robot 902, a surgical room layout, and changes to positions of a bed or equipment. An example operating room 102 including an surgical bed and example medical equipment is illustrated and described in more detail with reference to FIG. 1. The machine learning module 200 (illustrated and described in more detail with reference to FIG. 2) can be used to generate repositioning instructions for surgical robot 902 to optimize outcomes (determined based on simulations) for surgical steps.

A surgeon can indicate that a surgical tool such as an incision knife is required to be used at the left ankle of the patient and the surgical robot 902 would navigate the operating room using the markers to locate the left side of the patient and the relocate to the ankle level of the patient using the markers next to the operating table. In some embodiments, if the surgical robot 902 is in the wrong location the surgical robot 902 may use the markers to reposition itself to the correct position using the same method. In some embodiments, the user may input the [data?] if the surgical robot 902 is in the correct starting position, such as at a docking station located in the operating room, or the position in relation to the patient to confirm the surgical robot 902 is in the correct location. Then movement module 924 may determine if the current location of the surgical robot 902 is the correct location.

For example, the movement module 924 may determine the current location of the surgical robot 902 by using sensors from the mobility system 918 and compare the current location to the starting location stored in the received data entry from the base module 920 stored in the surgery database 928. In some embodiments, the user may input the [data?] if the surgical robot 902 is in the correct starting position, such as at a docking station located in the operating room, or the position in relation to the patient to confirm the surgical robot 902 is in the correct location. If it is determined that the current location of the surgical robot 902 is not correct the movement module 924 may alert the user. For example, if the surgical robot 902 is not in the correct location the movement module 924 may alert a user through a notification, such as a flashing light, a noise, or a message on the CAD GUI 942, etc.

Then the user may input the current location of the surgical robot 902 and the movement actions for the surgical robot 902. For example, the user may input the current location of the surgical robot 902 in the CAD GUI 942 and the movements required from the mobility system 918 to have the surgical robot 902 relocate to the desired position in the operating room. The movement module 924 executes, at step 1206, the movement action. For example, the movement module 924 executes the movement data file stored in the surgery database 928 which contains the required movement of the surgical robot 902 through the use of the mobility system 918 to relocate the surgical robot 902 to the required position.

In some embodiments, the movement of the surgical robot 902 may be from a data file containing the movement instructions of the surgical robot 902, such as 3 feet straight ahead, rotate 90 degrees, 2 feet straight ahead, etc. In some embodiments, the surgical robot 902 may use markers on the ground, such as QR codes, labels, arrows, etc. to identify a path to certain areas of the patient, such as left side head level, left side torso level, left side leg level, left side feet level, etc. Then the movement module 924 is continuously polling, at step 1208, for obstructions. For example, the movement module 924 is continuously receiving sensor data from the mobility system 918 in order to determine if there are any obstructions in the path of the surgical robot 902. For example, the mobility system 918 may be equipped with a plurality of sensors, such as image recognition devices, ultrasonic sensors, infrared sensors, etc. to detect objects that may be obstructing the surgical robots 902 path. In some embodiments, the mobility system 918 may be able to communicate with other surgical robots 902 or the medical staff to notify if the surgical robots 902 or medical staff are deemed to be an obstruction or if the surgical robot 902 itself is an obstruction.

The movement module 924 determines, at step 1210, if an obstruction was detected. For example, the movement module 924 is continuously receiving sensor data from the mobility system 918 in order to determine if there are any obstructions in the path of the surgical robot 902. For example, the mobility system 918 may be equipped with a plurality of sensors, such as image recognition devices, ultrasonic sensors, infrared sensors, etc. to detect objects that may be obstructing the surgical robots 902 path. In some embodiments, the mobility system 918 may be able to communicate with other surgical robots 902 or the medical staff to notify if the surgical robots 902 or medical staff are deemed to be an obstruction or if the surgical robot 902 itself is an obstruction.

If it is determined that an obstruction was detected then the movement module 924 alerts, at step 1212, the user. For example, if an obstruction is detected the movement module 924 may alert a user through a notification, such as a flashing light, a noise, a message on the CAD GUI 942, etc. to either alert the user of being an obstruction to the surgical robot 902 or to notify the user that the surgical robot is adjusting its course based on another type of obstruction, such as a medical light, table, chair, etc.

In embodiments, surgical robot 902 detects an obstruction to robotic arm 912 while surgical robot 902 is performing a surgical step. Surgical robot 902 indicates presence of the obstruction. Surgical robot 902 later determines absence of the obstruction. S.R.N 934 causes surgical robot 902 to continue performing the surgical step. If it is determined that an obstruction was not detected or after the user has been alerted and removed the obstruction the movement module 924 continues, at step 1214, executing the movement action. For example, the movement module 924 executes the movement data file stored in the surgery database 928 which contains the required movement of the surgical robot 902 through the use of the mobility system 918 to relocate the surgical robot 902 to the required position. In some embodiments, the movement of the surgical robot 902 may be from a data file containing the movement instructions of the surgical robot 902, such as 3 feet straight ahead, rotate 90 degrees, 2 feet straight ahead, etc.

In some embodiments, the surgical robot 902 may use markers on the ground, such as QR codes, labels, arrows, etc. to identify a path to certain areas of the patient, such as left side head level, left side torso level, left side leg level, left side feet level, etc. The movement module 924 determines, at step 1216, if the movement action is complete. If it is determined that the movement action is not complete, then the movement module 924 continues to poll for obstructions. If it is determined that the movement action is complete the movement module 924 sends, at step 1218, the completion status to the procedure module 926. For example, once the movement is complete the movement module 924 sends a completion status to the procedure module 926 in order to allow the procedure module 926 to extract the procedure data file and perform the necessary actions of the surgery. In some embodiments, the completion status may be stored in the surgery database 928. The movement module 924 returns, at step 9220, to the base module 920.

Figure 13:
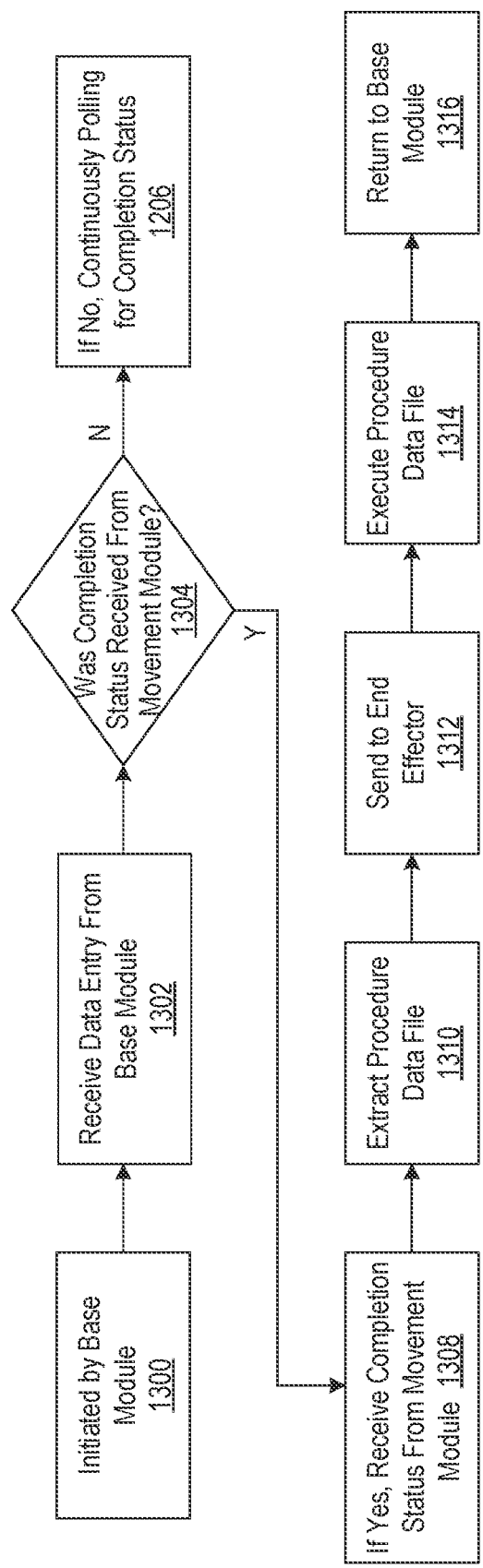
FIG. 13 illustrates a process for a procedure module, according to an embodiment.

FIG. 13 illustrates a process for a procedure module 926, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the procedure module 926. The process begins with the procedure module 926 being initiated, at step 1300, by the base module 920. The procedure module 926 receives, at step 1302, the extracted data entry from the base module 920. For example, the procedure module 926 receives the data entry such as the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

The procedure module 926 determines, at step 1304, if the completion status was received from the movement module 924. In some embodiments, the completion status may be stored in the surgery database 928. If the procedure module 926 determines that the completion status was not received from the movement module 924 then the procedure module 926 is continuously polling, at step 1306, to receive the completion status from the movement module 924 and returns to receiving the data entry from the base module 920. If the completion status was received then the procedure module 926 receives, at step 1308, the completion status from the movement module 924. For example, the procedure module 926 receives the completion status from the movement module 924. In some embodiments, the completion status may be stored in the surgery database 928.

The procedure module 926 extracts, at step 1310, the procedure data file from the data entry. For example, the procedure module 926 extracts the process or technique stored in the surgery database 928, such as mark spots on skin for anchors and suture locations on extensor retinaculum, make incision at distal point of fibula, use forceps to open incision, separate extensor retinaculum from fibula, etc. In some embodiments, the process or techniques are stored in order so that the extracted process or technique is the next step in an operation. The procedure module 926 sends, at step 1312, the procedure data file to the end effector 914. For example, the procedure module 926 sends the data file that contains the necessary movements of the end effector 914 to perform the necessary action of the surgery.

The procedure module 926 executes, at step 1314, the procedure data file. For example, for a procedure to stabilize an ankle the process stored in the surgery database 928 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint. For example, for the step of marking the location of the surgery the user may use a surgical skin marker tool in order to identify the specific locations on the patient for the incisions and other procedures such as the location of sutures, for example for a Brostrom-Gould repair surgery.

For example, the robotic arm 912 with an end effector 914 equipped with an incision knife may make an incision at the distal point of the fibula using the data file that contains the x, y, z coordinates of the patient's ankle as well as the necessary movements of the robotic arm 912. For example, the user may physically position a drill guide to determine the location of the anchors, and the end effector 914 with the drill may use the drill guide to insert the drill into the fibula and the end effector 914 with the drill is removed from the ankle leaving a location in the fibula for the anchor to be placed. Another end effector 914 with the anchor may use the drill guide to place an anchor in the fibula and when exiting the drill guide the end effector may hold the end of the suture, and the process may be repeated to place an anchor in the calcaneus bone. Then another end effector with a suture lasso may weave in and out of the extensor retinaculum ligament to create the suture holes for the suture from the anchor and a separate end effector 914 may loop the suture from the anchor into the suture lasso, which allows the end effector 914 with the suture lasso to pull leaving the suture from the anchor to be woven into the extensor retinaculum ligament, and this process may be repeated to reattach the ligament back to the bone. In some embodiments, the robotic arm 912 with end effectors 914 may perform the majority of the surgery. In some embodiments, the robotic arm 912 may be there to assist the surgeon or physician, such as drilling the holes for the anchors, placing the anchors, inserting the sutures into the ligament, etc. The procedure module 926 returns, at step 1316, to the base module 920.

FIG. 14 illustrates a surgery database 928, according to an embodiment. The database contains the patient's ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

In some embodiments, the database may contain staging areas for surgical robots 902 and active working areas and their corresponding range of motion. In some embodiments, the base and robotic arm 912 may be capable of moving independently such that when the base moves, the robotic arm can maintain its position and orientation, allowing the surgical robot 902 to make room for additional equipment or personnel or to increase the reach of the robot while not disrupting the procedure. In some embodiments, the surgical robots 902 may coordinate with multiple routines which allow the surgical robots 902 to stage out of the way and approach the operating table only when required. Routines may be preprogramed and triggered by a surgeon and the surgical robots 902 may navigate around the surgical staff and other equipment and may request other movable surgical robots 902 and surgical staff to move if necessary.

In some embodiments, if the user, such as the surgeon or physician, adjusts or updates the process or technique then the updated process or technique will be stored in the surgery database 928. For example, for a procedure to stabilize an ankle the process stored in the surgery database 928 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint.

Figure 15:
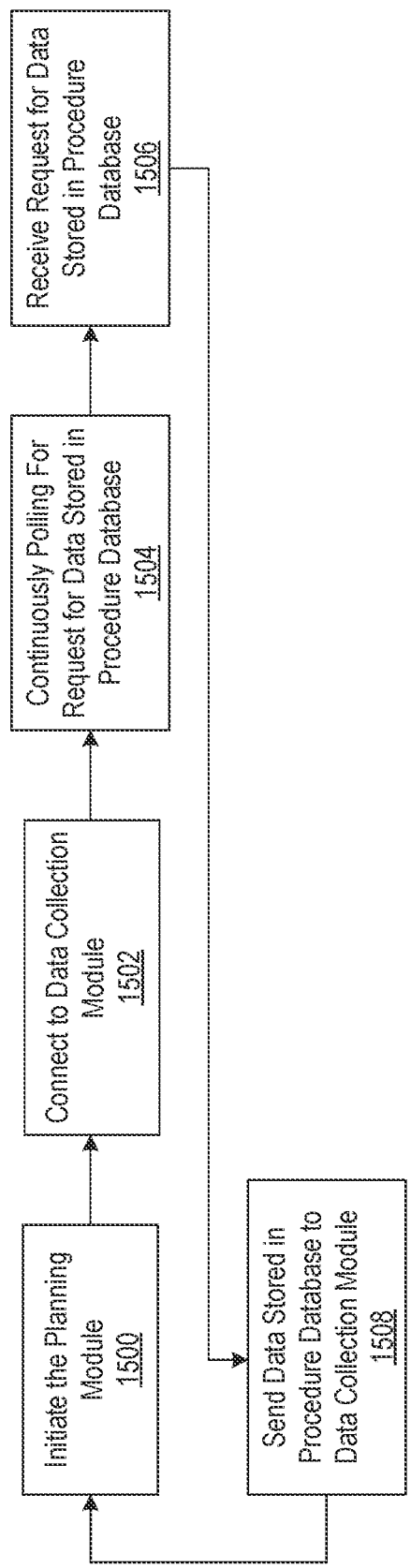
FIG. 15 illustrates a process for a S.R.N. base module, according to an embodiment.

FIG. 15 illustrates a process for a S.R.N. base module 936, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the S.R.N. base module 936. The process begins with the S.R.N. base module 936 initiating, at step 1500, the planning module 938. For example, the planning module 938 begins by being initiated by the S.R.N. base module 936. The planning module 938 queries the procedure database 940 for the first entry. The planning module 938 extracts the data entry from the procedure database 940. The planning module 938 displays the data entry on the CAD GUI 942. The user inputs the robotic movements and locations needed for the surgical robot 902 for the data entry. The planning module 938 stores the movements and locations in the procedure database 940. The planning module 938 determines if there are data entries remaining in the procedure database 940. If it is determined that there are data entries remaining in the procedure database 940 the planning module 938 queries the procedure database 940 for the next entry and continues to extract the data entry. If it is determined that there are no data entries remaining in the procedure database 940 the planning module 938 returns to the S.R.N. base module 936.

The S.R.N. base module 936 connects, at step 1502, to the data collection module 922. For example, the S.R.N. base module 936 connects to the data collection module 922 of the surgical robot 902 in order to pass along the procedure data that is necessary for the surgical robot 902 to move and perform functions of a surgery or assist a physician, surgeon, or medical professional in a surgical procedure. The S.R.N. base module 936 is continuously polling, at step 1504, for a request for the data stored in the procedure database 940. For example, the S.R.N. base module 936 is continuously polling to receive a request for data such as, the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

In some embodiments, the database may contain staging areas for surgical robots 902 and active working areas and their corresponding range of motion. In some embodiments, the base and robotic arm 912 may be capable of moving independently such that when the base moves, the robotic arm can maintain its position and orientation, allowing the surgical robot 902 to make room for additional equipment or personnel or to increase the reach of the robot while not disrupting the procedure. In some embodiments, the surgical robots 902 may coordinate with multiple routines which allow the surgical robots 902 to stage out of the way and approach the operating table only when required. Routines may be preprogramed and triggered by a surgeon and the surgical robots 902 may navigate around the surgical staff and other equipment and may request other movable surgical robots 902 and surgical staff to move if necessary.

In some embodiments, if the user, such as the surgeon or physician, adjusts or updates the process or technique then the updated process or technique will be stored in the procedure database 940. For example, for a procedure to stabilize an ankle the process stored in the procedure database 940 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint.

The S.R.N. base module 936 receives, at step 1506, a request for the data stored in the procedure database 940 from the data collection module 920. For example, the S.R.N. base module 936 receives a request for data, such as the patient's ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

In some embodiments, the database may contain staging areas for surgical robots 902 and active working areas and their corresponding range of motion. The base and robotic arm 912 can move independently such that when the base moves, the robotic arm can maintain its position and orientation, allowing the surgical robot 902 to make room for additional equipment or personnel or to increase the reach of the robot while not disrupting the procedure. In some embodiments, the robotic movement is based on a surgical plan. Surgical plans are described in more detail with reference to FIGS. 4A, 4B, and 5. The surgical plan can indicate an optimal location for planned surgical steps, functionality of surgical robot 902 (e.g., a range of motion or degrees of freedom), and/or surgical steps to be performed. In some embodiments, the surgical robots 902 may coordinate with multiple routines which allow the surgical robots 902 to stage out of the way and approach the operating table only when required. Routines may be preprogramed and triggered by a surgeon and the surgical robots 902 may navigate around the surgical staff and other equipment and may request other movable surgical robots 902 and surgical staff to move if necessary.

In some embodiments, if the user, such as the surgeon or physician, adjusts or updates the process or technique then the updated process or technique will be stored in the procedure database 940. For example, for a procedure to stabilize an ankle the process stored in the procedure database 940 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint.

The S.R.N. base module 936 sends, at step 1508, the data stored in the procedure database 940 to the data collection module 922 and returns to initiating the planning module 938. For example, the S.R.N. base module 936 sends data to the data collection module 922, such as the patient's ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques.

In some embodiments, the database includes staging areas for surgical robot 902, active working areas, and their corresponding range of motion. Robotic arm 912 can send a message to mobility system 918. The message indicates that a robotic surgical apparatus is performing a surgical step. Responsive to receiving the message, navigating of mobility system 918 is halted until the surgical step is complete.

In embodiments, mobility system 918 moves independently of robotic arm 912. For example, mobility system 918 and robotic arm 912 may be capable of moving independently such that when the base moves, the robotic arm can maintain its position and orientation, allowing the surgical robot 902 to make room for additional equipment or personnel or to increase the reach of the robot while not disrupting the procedure. Surgical robot 902 may coordinate with multiple routines which allows surgical robot 902 to stage out of the way and approach the operating table only when required. In embodiments, S.R.N. 934 causes mobility system 918 to navigate around surgical staff and equipment. Routines may be preprogramed and triggered by a surgeon and the surgical robots 902 may navigate around the surgical staff and other equipment and may request other movable surgical robots 902 and surgical staff to move if necessary.

In some embodiments, if the user, such as the surgeon or physician, adjusts or updates the process or technique then the updated process or technique will be stored in the procedure database 940. For example, for a procedure to stabilize an ankle the process stored in the procedure database 940 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint.

Figure 16:
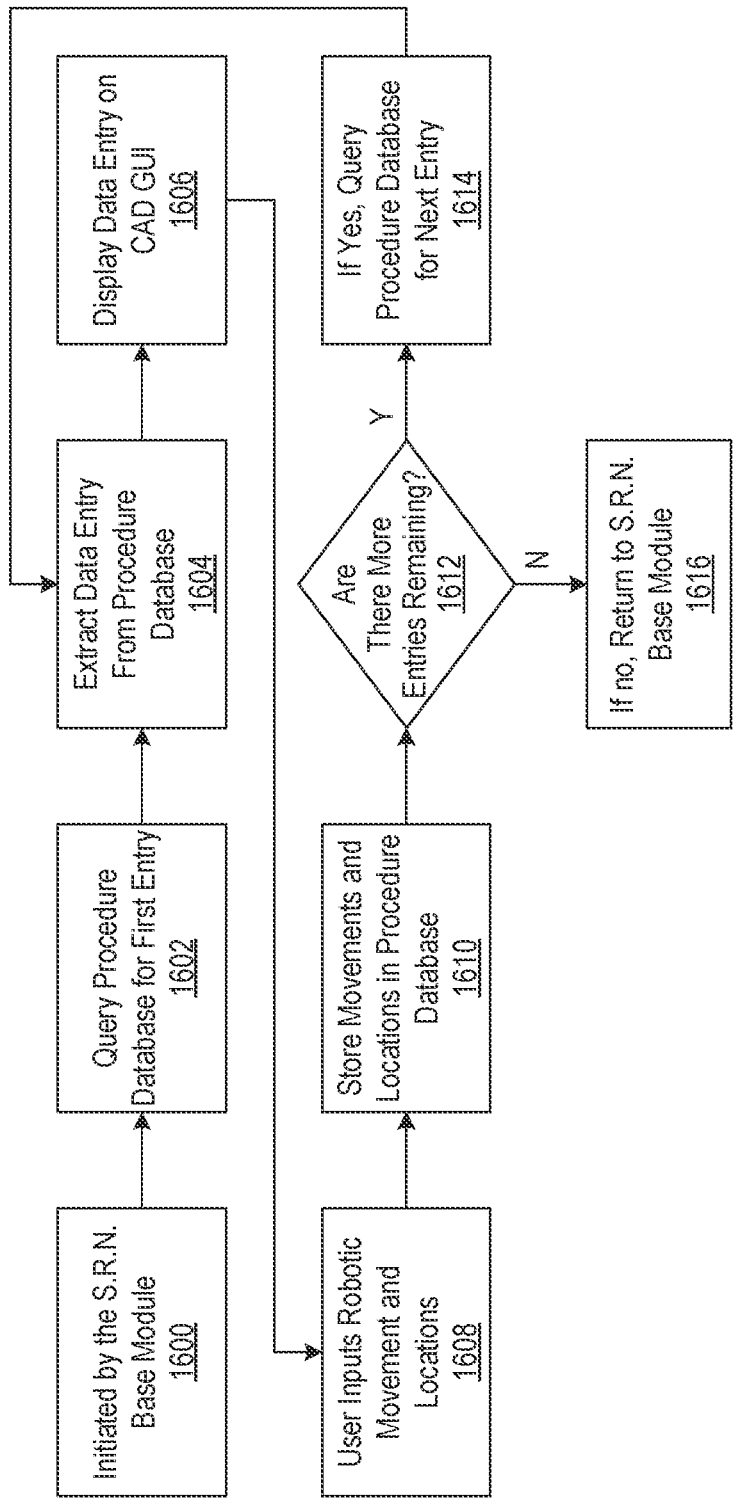
FIG. 16 illustrates a process for a planning module, according to an embodiment.

FIG. 16 illustrates a process for a planning module 938, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the planning module 938. The process begins with the planning module 938 being initiated, at step 1600, by the S.R.N. base module 936. The planning module 938 queries, at step 1602, the procedure database 940 for the first entry. For example, the planning module 938 queries the procedure database 940 for the first entry. The procedure database 940 may contain the patient ID, the type of surgery, the 3D image of the patient's medical images, the tools required for the surgery, the process required for the surgery, including the data files for replays of the step as inputted into the CAD GUI 944 and the x, y, z coordinates of the patient's body and the tools used, the techniques used, such as the threading technique used in the surgery, the calculations, such as the forces required in certain steps or techniques, the materials required for certain steps or techniques, and the specialists required for the specific steps or techniques.

In some embodiments, the procedure database 940 may be created from the user utilizing the CAD GUI 942 to perform the surgical procedure for a patient in a 3D environment including selecting the tools required for the surgery, the actions required from the surgical robot with the selected tools, and the data files containing the movements or actions of the surgical robot 902. The planning module 938 extracts, at step 1604, the data entry from the procedure database 940. For example, the planning module 938 extracts the first entry, such as the patient with the ID JS123, requires a Brostrom-Gould Repair Surgery, contains a 3D image of the patients ankle, and the first step in the surgical process is to mark spots on skin for anchors and suture locations on extensor retinaculum.

The planning module 938 displays, at step 1606, the data entry on the CAD GUI 942. For example, the planning module 938 displays the data entry with 3D image of the ankle on the CAD GUI 942. In some embodiments, the display may contain a replay of the step of the procedure performed, such as marking the spots on the patient's ankle, making an incision at the distal point of the fibula, etc. The user inputs, at step 1608, the robotic movements and locations needed for the surgical robot 902 for the data entry. For example, the operating room may be displayed on the CAD GUI 942 and the user may input the starting location of the surgical robot 902, such as in a docking position of the operating room, at the head of the patient, at the base of the patient, etc.

Navigation of surgical robot 902 can be based on camera images, LIDAR, or sensors incorporated into surgical robot 902 and/or surgical room layout to avoid hitting objects or personnel. Example cameras, sensors, and an operating room 102 are illustrated and described in more detail with reference to FIG. 1. The user may input the path required for the surgical robot 902 to take in order to be in position to perform the steps for the procedure. The user may input the ending location of the surgical robot 902 in relation to the patient, such as left side head level, left side torso level, left side leg level, left side foot level, etc. The user inputs may be stored as a data file for the instructions or program for mobility system 918 to position the surgical robot 902 in the correct position to perform the functions or action of the procedure required by the surgical robot 902. The mobility system 918 may comprises the elements required for movement, such as wheels 444 and at least one motor 442. The wheels 444 may be omnidirectional, tracks, etc. It may further comprise dedicated sensors, processing abilities, etc. and communicate with the rest of the surgical robot 902 systems to enable coordination with the at least one robotic arm.

The mobility system 918 may use user inputted data, from the CAD GUI 942, to determine the movements required of the surgical robot 902. In some embodiments, the movement of the surgical robot 902 may be from a data file containing the movement instructions of the surgical robot 902, such as 3 feet straight ahead, rotate 90 degrees, 2 feet straight ahead, etc. In some embodiments, the surgical robot 902 may use markers on the ground, such as QR codes, labels, arrows, etc. to identify a path to certain areas of the patient, such as left side head level, left side torso level, left side leg level, left side feet level, etc. In some embodiments, the mobility system 918 may be equipped with a plurality of sensors, such as image recognition devices, ultrasonic sensors, infrared sensors, etc. to detect objects that may be obstructing the surgical robots 902 path.

In some embodiments, the mobility system 918 may be able to communicate with other surgical robots 902 or the medical staff to notify if the surgical robots 902 or medical staff are deemed to be an obstruction or if the surgical robot 902 itself is an obstruction. In some embodiments, the surgical robot may receive user inputs for the position required for the surgical tool or end effectors and not receive user inputs to position itself throughout the operating room by using the sensors 916 and the mobility system 918. For example, there may be markers on the ground, such as QR codes, labels, arrows, etc. to identify a path to certain areas of the patient in which the surgical robot 902 reads the markers and can navigate the operating room to a final position either near or away from the patient depending on the need of the surgical robot 902.

For example, if the surgical robot is needed to be on the left side of the patient near the patient's leg there may be markers leading to the left side of the patient and once on the left side the markers may signal to the surgical robot the position relative to the patient, such as head level, upper chest level, lower chest level, upper abdomen level, lower abdomen level, hip level, femur level, knee level, chin or calf level, ankle level, foot level, etc. In this embodiment the surgical robot would not need user inputted navigation to locate and relocate around the patient during a surgical procedure in which the surgical robot 902 is needed.

The planning module 938 stores, at step 1610, the movements, and locations in the procedure database 940. For example, the data stored may be the user inputs, such as the starting location and the ending location of the surgical robot 902 in relation to the patient, such as left side head level, left side torso level, left side leg level, left side foot level, etc. In embodiments, a robotic surgical apparatus is caused to perform a surgical step at a location using end effector 914 and at least one of a portion of an anatomy of a patient or an instrument. The user inputs may be stored as a data file for the instructions or program for the mobility system 918 to position the surgical robot 902 in the correct position to perform the functions or action of the procedure required by the surgical robot 902.

In embodiments, mobility system 918 comprises at least one of an actuator, a wheel 444, a motor 442, or a sensor. Mobility system 918 may comprise the elements required for movement, such as a plurality of wheels and at least one motor. The wheels may be omnidirectional, tracks, etc. In embodiments, S.R.N. 934 causes mobility system 918 to communicate with robotic arm 912 to coordinate movement of mobility system 918 with robotic arm 912. Mobility system 918 can have dedicated sensors, processing abilities, etc. and communicate with the rest of the surgical robot 902 systems to enable coordination with the at least one robotic arm.

The mobility system 918 may use user inputted data, from the CAD GUI 942, to determine the movements required of the surgical robot 902. In some embodiments, the movement of the surgical robot 902 may be from a data file containing the movement instructions of the surgical robot 902, such as 3 feet straight ahead, rotate 90 degrees, 2 feet straight ahead, etc. In some embodiments, the surgical robot 902 may use markers on the ground, such as QR codes, labels, arrows, etc. to identify a path to certain areas of the patient, such as left side head level, left side torso level, left side leg level, left side feet level, etc. In some embodiments, surgical robot 902 detects, using at least one of an image recognition device, an ultrasonic sensor, or an infrared sensor, an object obstructing a path of mobility system 918. Surgical robot 902 indicates that the object is an obstruction. Mobility system 918 can be equipped with a plurality of sensors, such as image recognition devices, ultrasonic sensors, infrared sensors, etc. to detect objects that may be obstructing the surgical robots 902 path.

In some embodiments, mobility system 918 communicates with other surgical robots 902 or the medical staff to notify if the surgical robots 902 or medical staff are deemed to be an obstruction or if the surgical robot 902 itself is an obstruction. The planning module 938 determines, at step 1612, if there are data entries remaining in the procedure database 940. If it is determined that there are data entries remaining in the procedure database 940 the planning module 938 queries, at step 1614, the procedure database 940 for the next entry and continues to extract the data entry. For example, for any remaining data entries in the procedure database 940 the planning module 938 continues to query the next entry to allow the user to input the robotic movements and actions for each step for the surgical procedure until there are no remaining steps. If it is determined that there are data entries remaining in the procedure database 940 the planning module 938 returns, at step 1616, to the S.R.N. base module 936.

FIG. 17 illustrates a procedure database 940, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the procedure database 940. In embodiments, a first location, a second location, and a movement data file comprising movements for surgical robot 902 to move from the first location to the second location are stored. For example, database 940 contains the patient ID, the type of surgery, the 3D image of the patient's medical images, the starting position of the surgical robot 902, the ending location of the surgical robot 902, the movement data file which contains the movements required by the surgical robot 902 to move from the starting position to the ending position, the process required for the surgery, the techniques required for the surgery, the tools required for the surgery, the data file for the procedure or technique including the data files for replays of the step as inputted into the CAD GUI 942 and the x, y, z coordinates of the patient's body and the tools used, the techniques used, such as the threading technique used in the surgery, the data files for the robotic movements of the process or techniques, the calculations, such as the forces required in certain steps or techniques, the materials required for certain steps or techniques, and the specialists required for the specific steps or techniques. In some embodiments, the database describes a staging area for surgical robot 902, a working area for surgical robot 902, and a range of motion for surgical robot 902. For example, the database contains staging areas for surgical robots 902 and active working areas and their corresponding range of motion.

In some embodiments, robotic arm 912 has at least two degrees of freedom. Robotic arm 912 can move independently such that when the base moves, the robotic arm can maintain its position and orientation, allowing the surgical robot 902 to make room for additional equipment or personnel or to increase the reach of the robot while not disrupting the procedure. In some embodiments, the surgical robots 902 may coordinate with multiple routines which allow the surgical robots 902 to stage out of the way and approach the operating table only when required. Surgical robot 902 can execute instructions received from S.R.N. 934 or cloud 932 to navigate a mobile unit within an operating room. Navigating the mobile unit causes a robotic surgical apparatus to move from a first location to a second location. Routines may be preprogramed and triggered by a surgeon and the surgical robots 902 may navigate around the surgical staff and other equipment and may request other movable surgical robots 902 and surgical staff to move if necessary. In embodiments, S.R.N. 934 generates instructions to move surgical robots 902, using a machine learning module, based on a first location, a second location, and a location of at least one of a portion of an anatomy of a patient or an instrument.

In some embodiments, if the user, such as the surgeon or physician, adjusts or updates the process or technique then the updated process or technique will be stored in the procedure database 940. For example, for a procedure to stabilize an ankle the process stored in the procedure database 940 may be that the patient is prepped and draped. Arthroscopic debridement takes place of the ankle joint. An incision is made from the tip of the fibula to the extensor retinaculum. A drill hole is made into the calcaneus and an anchor is placed. Suture is then sewn into the extensor retinaculum. A drill hole is made into the fibula and an anchor is placed. The suture limbs from the anchors are tied to bring the ankle mortise into neutral position to stabilize the ankle joint.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A computer-implemented method for control and navigation of a robotic surgical apparatus, the method comprising:
    positioning, by a computer system, the robotic surgical apparatus at a first location in an operating room,
        wherein the robotic surgical apparatus comprises a mobile unit configured to move the robotic surgical apparatus, a robotic arm, and an end effector attached to the robotic arm;
    determining one or more instruments are available for performing at least a portion of a surgical step to be performed on a portion of an anatomy of a patient;
    determining at least one outcome of a pre-operative simulation with the one or more instruments and the end effector, when the robotic surgical apparatus is positioned at the first location, wherein the pre-operative simulation indicates that the end effector is unable to use the one or more instruments to perform the portion of the surgical step;
    receiving instructions to move the robotic surgical apparatus from the first location to a second location in the operating room;
    executing the instructions to navigate the mobile unit within the operating room,
        wherein navigating the mobile unit causes the robotic surgical apparatus to move from the first location to the second location; and
    causing the robotic surgical apparatus to perform the surgical step at the second location using the end effector and the one or more instruments.

2. The method of claim 1,
    wherein the surgical step is a first surgical step, the method comprising:
    causing the robotic arm to send a message to the mobile unit,
        wherein the message indicates that the robotic surgical apparatus is performing a second surgical step; and
        responsive to receiving the message, halting navigating of the mobile unit until the second surgical step is complete.

3. The method of claim 1, wherein navigating the mobile unit comprises:
    causing the robotic arm and the end effector to remain stationary while the robotic surgical apparatus moves from the first location to the second location, and/or
    moving a table supporting the patient relative to the robotic arm.

4. The method of claim 1, wherein the mobile unit comprises at least one of:
    an actuator, a wheel, a motor, or a sensor.

5. The method of claim 1, comprising:
    causing the mobile unit to communicate with the robotic arm to coordinate movement of the mobile unit with the robotic arm.

6. The method of claim 1, wherein a portion of the instructions are indicated by a user using a computer-aided design (CAD) graphical user interface.

7. The method of claim 1, wherein navigating the mobile unit comprises:
    causing the mobile unit to determine a path to at least one of the portion of the anatomy or the one or more instruments using at least one of quick response (QR) codes, labels, or arrows posted on a surface of the operating room.

8. A computer system for control and navigation of a robotic surgical apparatus, the computer system comprising a non-transitory computer-readable storage medium storing computer code, which when executed by one or more computer processors causes the computer system to:
    position the robotic surgical apparatus at a first location in an operating room,
        wherein the robotic surgical apparatus comprises a mobile unit configured to move the robotic surgical apparatus, a robotic arm, and an end effector attached to the robotic arm;
    determine one or more instruments are available for performing at least a portion of a surgical step to be performed on a portion of an anatomy of a patient;
    determine at least one outcome of a pre-operative simulation with the one or more instruments and the end effector, when the robotic surgical apparatus is positioned at the first location, wherein the pre-operative simulation indicates that the end effector is unable to use the one or more instruments to perform the portion of the surgical step;
    receive instructions to move the robotic surgical apparatus from the first location to a second location in the operating room;
    execute the instructions to navigate the mobile unit within the operating room,
        wherein navigating the mobile unit causes the robotic surgical apparatus to move from the first location to the second location; and
    cause the robotic surgical apparatus to perform the surgical step at the second location using the end effector and the one or more instruments.

9. The computer system of claim 8,
    wherein the surgical step is a first surgical step, and
    wherein the computer code causes the computer system to:
    cause the robotic arm to send a message to the mobile unit, wherein the message indicates that the robotic surgical apparatus is performing a second surgical step; and responsive to receiving the message, halt navigating of the mobile unit until the second surgical step is complete.

10. The computer system of claim 8, wherein the computer code to navigate the mobile unit causes the robotic arm and the end effector to remain stationary while the robotic surgical apparatus moves from the first location to the second location.

11. The computer system of claim 8, wherein the mobile unit comprises at least one of:

an actuator, a wheel, a motor, or a sensor.

12. The computer system of claim 8, wherein the computer code causes the mobile unit to communicate with the robotic arm to coordinate movement of the mobile unit with the robotic arm.

13. The computer system of claim 8, wherein a portion of the instructions indicated by a user using a computer-aided design (CAD) graphical user interface.

14. The computer system of claim 8, wherein the computer code to navigate the mobile unit causes the mobile unit to determine a path to at least one of the portion of the anatomy or the one or more instruments using at least one of quick response (QR) codes, labels, or arrows posted on a surface of the operating room.

15. A non-transitory computer-readable storage medium storing computer code, which when executed by one or more computer processors causes the one or more computer processors to:

position a robotic surgical apparatus at a first location in an operating room,
    wherein the robotic surgical apparatus comprises a mobile unit configured to move the robotic surgical apparatus, a robotic arm, and an end effector attached to the robotic arm;

determine one or more instruments are available for performing at least a portion of a surgical step to be performed on a portion of an anatomy of a patient;

determine at least one outcome of a pre-operative simulation with the one or more instruments and the end effector when the robotic surgical apparatus is positioned at the first location, wherein the pre-operative simulation indicates that the end effector is unable to use the one or more instruments to perform the portion of the surgical step;

receive instructions to move the robotic surgical apparatus from the first location to a second location in the operating room;

execute the instructions to navigate the mobile unit within the operating room,
    wherein navigating the mobile unit causes the robotic surgical apparatus to move from the first location to the second location; and cause the robotic surgical apparatus to perform the surgical step at the second location using the end effector and the one or more instruments.

16. The non-transitory computer-readable storage medium of claim 15, wherein the surgical step is a first surgical step, and wherein the computer code causes the one or more computer processors to:

cause the robotic arm to send a message to the mobile unit,
    wherein the message indicates that the robotic surgical apparatus is performing a second surgical step; and responsive to receiving the message, halt navigating of the mobile unit until the second surgical step is complete.

17. The non-transitory computer-readable storage medium of claim 15, wherein the computer code to navigate the mobile unit causes at least one of:

the robotic arm and the end effector to remain stationary while the robotic surgical apparatus moves from the first location to the second location, or moving of a table supporting the patient to move the patient relative to the robotic arm.

18. The non-transitory computer-readable storage medium of claim 15, wherein the mobile unit comprises at least one of:

an actuator, a wheel, a motor, or a sensor.

19. The non-transitory computer-readable storage medium of claim 15, wherein the computer code causes the mobile unit to communicate with the robotic arm to coordinate movement of the mobile unit with the robotic arm.

20. The non-transitory computer-readable storage medium of claim 15, wherein a portion of the instructions indicated by a user using a computer-aided design (CAD) graphical user interface.

* * * * *